(12) United States Patent
Pfaendner et al.

(10) Patent No.: US 10,544,284 B2
(45) Date of Patent: Jan. 28, 2020

(54) USE OF PHOSPHOROUS-CONTAINING ORGANIC OXYIMIDES AS FLAME RETARDANTS AND/OR AS STABILIZERS FOR PLASTICS, FLAME-RETARDANT AND/OR STABILIZED PLASTIC COMPOSITIONS, METHOD FOR THE PRODUCTION THEREOF, MOULDED PART, PAINT AND COATINGS

(71) Applicant: FRAUNHOFER-GESELLSCHAFT ZUR FÖRDERUNG DER ANGEWANDTEN FORSCHUNG E.V., München (DE)

(72) Inventors: Rudolf Pfaendner, Rimbach (DE); Markus Mazurowski, Ginsheim-Gustav (DE)

(73) Assignee: Fraunhofer-Gesellschaft zur förderung der angewandten Forschung e.V., München (DE)

( * ) Notice: Subject to any disclaimer, the term of this patent is extended or adjusted under 35 U.S.C. 154(b) by 135 days.

(21) Appl. No.: 15/511,445

(22) PCT Filed: Sep. 16, 2015

(86) PCT No.: PCT/EP2015/071251
§ 371 (c)(1),
(2) Date: Mar. 15, 2017

(87) PCT Pub. No.: WO2016/042040
PCT Pub. Date: Mar. 24, 2016

(65) Prior Publication Data
US 2017/0260366 A1    Sep. 14, 2017

(30) Foreign Application Priority Data
Sep. 18, 2014  (DE) .................. 10 2014 218 811

(51) Int. Cl.

| | |
|---|---|
| C08K 5/3417 | (2006.01) |
| C08K 5/5313 | (2006.01) |
| C08K 5/00 | (2006.01) |
| C08K 5/5373 | (2006.01) |
| C08K 3/00 | (2018.01) |
| C08K 5/17 | (2006.01) |
| C08K 5/20 | (2006.01) |
| C08K 5/23 | (2006.01) |
| C08K 5/32 | (2006.01) |
| C08K 5/3412 | (2006.01) |
| C08K 5/49 | (2006.01) |
| C08K 5/52 | (2006.01) |
| C08K 5/53 | (2006.01) |
| C08K 5/5353 | (2006.01) |
| C08L 101/00 | (2006.01) |
| C08L 23/12 | (2006.01) |
| C08L 23/06 | (2006.01) |
| C08L 85/02 | (2006.01) |

(Continued)

(52) U.S. Cl.
CPC ........ *C08K 5/5373* (2013.01); *B29C 45/0001* (2013.01); *B29C 48/022* (2019.02); *C07F 9/5728* (2013.01); *C08K 5/32* (2013.01); *C08K 5/3412* (2013.01); *C08K 5/3417* (2013.01); *C08K 5/49* (2013.01); *C08K 5/52* (2013.01); *C08K 5/53* (2013.01); *C08K 5/5313* (2013.01); *C08K 5/5353* (2013.01); *C09D 5/18* (2013.01); *C09D 123/12* (2013.01); *C09K 15/30* (2013.01); *C09K 15/322* (2013.01); *C09K 21/12* (2013.01); *B29K 2023/06* (2013.01); *B29K 2023/12* (2013.01); *B29K 2105/0005* (2013.01)

(58) Field of Classification Search
CPC .......... C08K 5/32; C08K 5/34; C08K 5/3412; C08K 5/3415; C08K 5/3417; C08K 5/49–5399; C09K 21/10; C09K 21/12; C09K 15/30; C07F 9/5728
See application file for complete search history.

(56) References Cited

U.S. PATENT DOCUMENTS 2,682,522 A  6/1954  Coover et al.
2,716,101 A  8/1955  Coover et al.
(Continued)

FOREIGN PATENT DOCUMENTS

CN   1968744 A   5/2007
CN   101258194 A   9/2008
(Continued)

OTHER PUBLICATIONS

Translation of JP S50-064338 A.*
(Continued)

*Primary Examiner* — Kregg T Brooks
(74) *Attorney, Agent, or Firm* — Leydig, Voit & Mayer, Ltd.

(57) ABSTRACT

The present invention relates to the use of phosphorous-containing organic oxyimides according to the general formula (I) as flame retardant for plastic materials, as radical generators in plastic materials and/or stabilisers for plastics. In addition, the present invention relates to a flame-retardant plastic material moulding compound in which the previously described phosphorous-containing organic oxyimides are integrated, and also to a method for the production of the previously mentioned plastic material composition. Furthermore, the present invention relates to a moulded article, a paint or a coating from the previously mentioned flame-retardant plastic material composition.

16 Claims, No Drawings

(51) Int. Cl.
| | | |
|---|---|---|
| C09D 5/18 | (2006.01) | |
| C09D 123/12 | (2006.01) | |
| C09D 201/00 | (2006.01) | |
| C07F 9/572 | (2006.01) | |
| C07F 9/02 | (2006.01) | |
| C09K 15/30 | (2006.01) | |
| C09K 15/32 | (2006.01) | |
| C09K 21/12 | (2006.01) | |
| B29C 45/00 | (2006.01) | |
| B29C 47/00 | (2006.01) | |
| C07D 211/58 | (2006.01) | |
| C07D 251/34 | (2006.01) | |
| C08F 2/38 | (2006.01) | |
| C08F 4/32 | (2006.01) | |
| C08F 8/00 | (2006.01) | |
| C08F 8/50 | (2006.01) | |
| C08G 79/04 | (2006.01) | |
| B29C 48/00 | (2019.01) | |
| B29K 23/00 | (2006.01) | |
| B29K 105/00 | (2006.01) | |

(56) References Cited

U.S. PATENT DOCUMENTS

| | | | |
|---|---|---|---|
| 2,891,915 | A | 6/1959 | McCormack et al. |
| 3,326,852 | A | 6/1967 | Thomas |
| 3,442,854 | A | 5/1969 | Curtius et al. |
| 3,919,363 | A | 11/1975 | Ura et al. |
| 3,946,093 | A | 3/1976 | Koto et al. |
| 3,960,885 | A | 6/1976 | Keihs et al. |
| 4,003,862 | A | 1/1977 | Albright et al. |
| 4,267,084 | A | 5/1981 | Mizutani et al. |
| 4,328,174 | A | 5/1982 | Schmidt et al. |
| 4,331,614 | A | 5/1982 | Schmidt et al. |
| 4,374,971 | A | 2/1983 | Schmidt et al. |
| 4,409,367 | A | 10/1983 | Beijleveld et al. |
| 4,415,719 | A | 11/1983 | Schmidt et al. |
| 5,216,113 | A | 6/1993 | Schulz-Schlitte et al. |
| 5,334,692 | A | 8/1994 | Hess et al. |
| 6,288,210 | B1 | 9/2001 | Shobha et al. |
| 6,291,630 | B1 | 9/2001 | König et al. |
| 6,861,499 | B2 | 3/2005 | Vinciguerra et al. |
| 7,816,486 | B2 | 10/2010 | Freitag et al. |
| 9,428,692 | B2 | 8/2016 | Okada et al. |
| 9,505,541 | B2 | 11/2016 | Menozzi et al. |
| 10,370,537 | B2 | 8/2019 | Pfaendner et al. |
| 2005/0020800 | A1 | 1/2005 | Levchik et al. |
| 2005/0148701 | A1* | 7/2005 | Harashina ............ C08K 5/5399 524/95 |
| 2007/0219295 | A1 | 9/2007 | Levchik et al. |
| 2008/0045673 | A1 | 2/2008 | Piotrowski et al. |
| 2008/0061270 | A1 | 3/2008 | Tsuji et al. |
| 2008/0269383 | A1 | 10/2008 | Pauquet et al. |
| 2009/0286060 | A1 | 11/2009 | Sala et al. |
| 2013/0023609 | A1 | 1/2013 | Menozzi et al. |
| 2014/0225034 | A1 | 8/2014 | Okada et al. |
| 2015/0217923 | A1 | 8/2015 | Menozzi et al. |
| 2016/0052927 | A1 | 2/2016 | Pfaendner et al. |
| 2016/0272789 | A1 | 9/2016 | Pfaendner et al. |
| 2017/0043931 | A1 | 2/2017 | Menozzi et al. |
| 2017/0107375 | A1 | 4/2017 | Pfaendner et al. |
| 2017/0121499 | A1 | 5/2017 | Pfaendner et al. |
| 2017/0260362 | A1 | 9/2017 | Pfaendner et al. |
| 2017/0260363 | A1 | 9/2017 | Pfaendner et al. |
| 2017/0267835 | A1 | 9/2017 | Groos et al. |
| 2018/0186970 | A1 | 7/2018 | Groos et al. |
| 2018/0282046 | A1 | 10/2018 | Menozzi et al. |
| 2019/0248927 | A1 | 8/2019 | Klein et al. |

FOREIGN PATENT DOCUMENTS

| | | |
|---|---|---|
| CN | 103764259 A | 4/2014 |
| DE | 102013005307 A1 | 9/2014 |
| DE | 102014210214 A1 | 12/2015 |
| GB | 801523 A | 9/1958 |
| JP | 41-20234 B | 11/1966 |
| JP | 50-64338 A | 5/1975 |
| JP | S57-139130 A | 8/1982 |
| JP | 2009-507116 A | 2/2009 |
| JP | 2009-102621 A | 5/2009 |
| JP | 2013-512977 A | 4/2013 |
| WO | WO 99/00450 A1 | 1/1999 |
| WO | WO 01/90113 | 11/2001 |
| WO | WO 03/070736 A1 | 8/2003 |
| WO | WO 2005/030852 A2 | 4/2005 |
| WO | WO 2006/084488 A1 | 8/2006 |
| WO | WO 2006/084489 A1 | 8/2006 |
| WO | WO 2006/106059 A1 | 10/2006 |
| WO | WO 2007/028731 A1 | 3/2007 |
| WO | WO 2008/101845 A1 | 8/2008 |
| WO | WO 2010/135398 A1 | 11/2010 |
| WO | WO 2011/000019 A1 | 1/2011 |
| WO | WO 2011/067197 A2 | 6/2011 |
| WO | WO 2012/000022 A1 | 1/2012 |
| WO | WO 2013/020696 A2 | 2/2013 |
| WO | WO 2013/068437 A2 | 5/2013 |
| WO | WO 2013/072295 A1 | 5/2013 |
| WO | WO 2014/064064 A1 | 5/2014 |
| WO | WO 2014/154636 A1 | 10/2014 |
| WO | WO 2015/180888 A1 | 12/2015 |

OTHER PUBLICATIONS

Aubert et al., "Azoalkanes—novel flame retardants and their structure-property relationship," *Polym. Adv. Technol.* 22(11): 1529-1538 (2011).

Aubert et al., "Azoalkanes—A Novel Class of Additives for Cross-Linking and Controlled Degradation of Polyolefins," *Macromolecular Materials and Engineering.* 292: 707-714 (2007).

Pawelec et al., "Triazene compounds as a novel and effective class of flame retardants for polypropylene," *Polym. Degrad. Stab.* 87(6): 948-954 (2012).

Wilén et al., "Improving weathering resistance of flame-retarded polymers," *Journal of Applied Polymer Science* 129(3):925-944 (2013).

European Patent Office, International Search Report and Written Opinion issued in International Application No. PCT/EP2015/071251 (dated Nov. 27, 2015).

International Bureau of WIPO, International Preliminary Report on Patentability issued in International Application No. PCT/EP2015/071251 (dated Mar. 21, 2017).

State Intellectual Property Office of the People's Republic of China, First Office Action and Search Report issued in Chinese Patent Application No. 2015800502829 (dated Jun. 21, 2018).

Aubert et al., "Versatile bis(1-alkoxy-2,2,6,6-tetramethylpiperidin-4-yl)-diazenes (AZONORs) and related structures and their utilization as flame retardants in polypropylene, low density polyethylene and high-impact polystyrene,", *Polymer Degradation and Stability* 97(8): 1438-1446 (2012).

Nicolas et al., "Azoalkanes: A Novel Class of Flame Retardants," *Macromolecular Rapid Communications* 27(12): 976-981 (2006).

Tirri et al., "Novel tetrapotassium azo diphosphonate (INAZO) as flame retardant for polyurethane adhesives," *Polymer Degradation and Stability* 97(3): 375-382 (2012).

Sui et al., *Light Stabilizer and Its Application Technology*, China Light Industry Press, 2010, pp. 11-12.

China National Intellectual Property Administration, Second Office Action in Chinese Patent Application No. 2015800502829 (dated Feb. 3, 2019).

European Patent Office, Notification under Article 94 (3) EPC in European Patent Application No. 15 771 537.6 (dated Apr. 15, 2019; received Apr. 16, 2019).

U.S. Appl. No. 14/779,849, filed Sep. 24, 2015.
U.S. Appl. No. 15/311,674, filed Nov. 16, 2016.
U.S. Appl. No. 15/511,410, filed Mar. 15, 2017.
U.S. Appl. No. 15/511,471, filed Mar. 15, 2017.
U.S. Appl. No. 15/738,515, filed Dec. 20, 2017.

(56) References Cited

OTHER PUBLICATIONS

U.S. Appl. No. 16/344,830, filed Apr. 25, 2019.
U.S. Appl. No. 16/488,902, filed Aug. 26, 2019.
Chemical Abstracts Registry No. 30974-04-0, Registry/STN (Nov. 16, 2014).
*Plastics Additives Handbook*, 5th edition, Hans Zweifel, Editor, Hanser Publishers, Munich, pp. 725-811 (2001).
German Patent and Trademark Office, Office Action in German Patent Application No. 10 2014 218 811.3 (dated Mar. 24, 2015).
State Intellectual Property Office of People'S Republic of China, First Office Action in Chinese Patent Application No. 201580050105.0 (dated Jun. 21, 2018).
China National Intellectual Property Administration, Second Office Action in Chinese Patent Application No. 201580050105.0 (dated Feb. 3, 2019).
European Patent Office, Notification under Article 94 (3) EPC in European Patent Application No. 15 771 536.8 (dated Apr. 15, 2019).
Japan Patent Office, Notification of Reasons for Refusal in Japanese Patent Application No. 2017-515052 (dated May 22, 2019).
European Patent Office, International Search Report in International Application No. PCT/EP2015/071249 (dated Nov. 27, 2015).
European Patent Office, Written Opinion in International Application No. PCT/EP2015/071249 (dated Nov. 27, 2015).
International Bureau of WIPO, International Preliminary Report on Patentability in International Application No. PCT/EP2015/071249 (dated Mar. 21, 2017).

* cited by examiner

USE OF PHOSPHOROUS-CONTAINING ORGANIC OXYIMIDES AS FLAME RETARDANTS AND/OR AS STABILIZERS FOR PLASTICS, FLAME-RETARDANT AND/OR STABILIZED PLASTIC COMPOSITIONS, METHOD FOR THE PRODUCTION THEREOF, MOULDED PART, PAINT AND COATINGS

CROSS-REFERENCE TO RELATED APPLICATIONS

This patent application is the U.S. national phase of International Application No. PCT/EP2015/071251, filed on Sep. 16, 2015, which claims the benefit of German Patent Application No. 10 2014 218 811.3, filed Sep. 18, 2014, the disclosures of which are incorporated herein by reference in their entireties for all purposes.

The present invention relates to the use of phosphorus-containing organic oxyimides according to the general formula I illustrated below as flame retardant for plastic materials and/or as stabilisers for plastic materials. In addition, the present invention relates to a flame-retardant plastic material moulding compound in which the previously described phosphorus-containing organic oxyimides are integrated, and also to a method for the production of the previously mentioned plastic material composition. In addition, the invention relates to a stabilised plastic material composition. Furthermore, the present invention relates to a moulded article, a paint or a coating made of the previously mentioned flame-retardant plastic material composition.

Most plastic materials are combustible and comparatively easily inflammable. In order to reduce or exclude the risk of fire to plastic materials in specific applications, it is therefore absolutely necessary to reduce the flammability and to use flameproof plastic material compositions. For this purpose, generally flame retardants are added to the plastic material with the aim of preventing ignition for a specific time or significantly reducing the spread of fire. Traditional flame retardants are based on chlorine- and bromine-containing compounds (the latter generally in combination with antimony trioxide), on phosphorus-containing, on nitrogen-containing compounds and on metal hydroxides, such as aluminium hydroxide (ATH) or magnesium hydroxide (MDH). In more recent times, halogen-free flame-retardant solutions are preferred on toxicological and ecotoxicological grounds.

For the production of flame-retardant plastic materials, there is a large number of flame retardants which are used generally substrate-specifically for a specific polymer and a specific field of use, corresponding to the standards which form the basis thereof. Flame-retardant plastic materials are used for example in electrical and electronic applications, in the transport field (trains, aircraft, cars), in textiles and in construction.

A new flame-retardant class, developed in the last few years, based on nitrogen, preferably for polyolefins, is based on selected alkoxyamines (e.g. WO 99/00450). Due to cleavage of the alkoxyamines, radicals are produced in the case of fire, which radicals become involved in the decomposition process of the polymer and hence cause the flame-retardant effect (C. R. Wilen, R. Pfaendner, J. Appl. Pol. Sci. 2013, 129, 925-944). Apart from alkoxyamines, in the meantime, also other radical generators have been described, which act as flame retardants or as flame-retardant synergists, such as azo compounds (Nicolas et al. Macromol. Rapid Commun. 2006, 27, 976-981, WO 2005/030852), hydrazones and azines (M. Aubert et al., Pol. Adv. Technol. 2011, 22, 1529-1538), azo-alkoxyamines (M. Aubert et al. Pol. Degr. Stab. 2012, 97, 1438-1446) azo-phosphonates (T. Tirri et al., Pol. Degr. Stab. 2012, 97, 375-382) or triazenes (W. Pawelec et al., Pol. Degr. Stab. 2012, 97, 948-954).

Furthermore, the use of new radical generators based on hydroxyimides and polymeric imides as flame retardant is described in DE 10 2013 005 307 or DE 10 2014 210 214.

These classes of compounds are preferably used in combination with other flame retardants, e.g. based on other nitrogen-, phosphorus-, halogen- or sulphur-containing compounds, since as a result synergistic combinations are produced. One disadvantage of the combinations is, however, that more than one compound is used, which e.g. can increase the licensing costs, an additional source of error results and undesired interactions between the components, such as e.g. chemical reactions, can occur.

It was therefore the object of the present invention to make available new flame retardants and synergistic flame-retardant components based on radical generators which are very effective. Furthermore, selected compounds can be used as stabilisers for plastic materials.

This object is achieved by the use of a phosphorus-containing organic oxyimide described herein, by a flame-retardant and/or stabilised plastic material composition having the features described herein, by a method for the production of the flame-retardant and/or stabilised plastic material composition described herein, and also by a moulded part, a paint or a coating having the features described. Also described are advantageous developments of the invention.

The invention hence relates to the use of phosphorus-containing organic oxyimides, containing at least one structural element of subsequently illustrated formula I

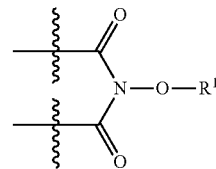

Formula I $R^1$ being selected from the group consisting of phosphorus-containing radicals,
as flame retardant for plastic materials, as stabilisers for plastic materials and/or as antioxidants for plastic materials.

It has now been shown that, by means of molecules which comprise both the oxyimide group and at least one phosphorus group, the flame-retardant effect of the oxyimides can be further increased. These selected structures have to date not been explicitly included by the individual applications indicated above. At the same time, many of these products are producible inexpensively from starting compounds which are available on a large scale.

The group $R^1$ contained in the phosphorus-containing organic oxyimide illustrated above thereby comprises at least one phosphorus atom. The group $R^1$ can thereby also represent a radical which comprises a plurality of phosphorus atoms. In particular, it is possible that the structure according to formula I is repeated, i.e. a plurality of the illustrated oxyimide groups are present in the molecule.

The object of making available new flame retardants and flame-retardant components with high effectiveness is preferably achieved by using compounds which comprise both at least one oxyimide group and at least one phosphorus group in the molecule, i.e. at least one structural unit of the general formulae Ia, Ib, Ic, with the proviso that these structures do not comprise any halogens.

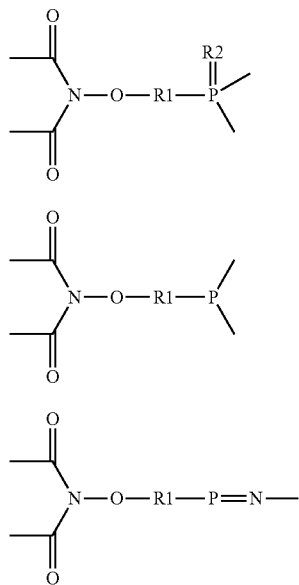

Ia

Ib

Ic

R1 is a direct bond, a possibly substituted alkyl-, cycloalkyl-, aryl- or heteroaryl group, which comprises no halogen.

R2 is O or S

According to the invention, it is preferred if the group R1 indicated above in formula I is selected from the group consisting of

—X—Y

X meaning a direct chemical bond, an unsubstituted or substituted alkylene radical, an unsubstituted or substituted cycloalkylene radical, an unsubstituted or substituted aryl radical, an unsubstituted or substituted heteroaryl radical or an acyl group, the carbonyl radical of which is bonded to the oxygen atom and the acid radical of which is bonded to Y, and Y meaning a phosphorus-containing grouping which is chemically crosslinked to X via the phosphorus atom, and in which the phosphorus atom has the valency −3 to 5, in particular −2, −1, 0, +1, +2, +3, +4 or +5.

In the above-indicated grouping X—Y, it is advantageous if the radical Y is selected from the group consisting of the subsequently illustrated groupings

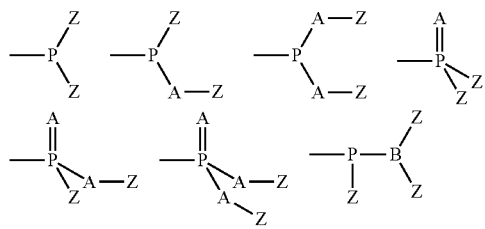

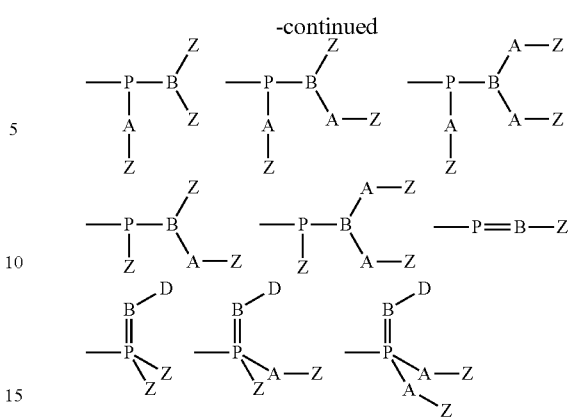

-continued

Z upon each occurrence, being the same or different and being selected from the group consisting of linear or branched and/or unsubstituted or substituted alkyl radicals, unsubstituted or substituted aryl radicals, unsubstituted or substituted heteroaryl radicals or acyl groups, the carbonyl radical of which is bonded to the phosphorus atom or A or B, the previously mentioned radicals being able to be substituted by at least one further structural element according to the above-illustrated formula I and/or by at least one further radical R1 and also from structural elements of the above-illustrated formula I and groupings —X—Y, A upon each occurrence, being the same or different and meaning oxygen or sulphur, B upon each occurrence, being the same or different and meaning nitrogen, and D upon each occurrence, being the same or different and being selected from the group consisting of linear or branched and/or unsubstituted or substituted alkyl radicals, unsubstituted or substituted aryl radicals, unsubstituted or substituted heteroaryl radicals, the previously mentioned radicals being able to be substituted possibly by at least one further structural element according to the above-illustrated formula I and/or by at least one further radical R1.

In particular the phosphorus-containing organic oxyimide is halogen-free, i.e. the corresponding compound comprises no halogen atoms.

Preferred phosphorus-containing organic oxyimides have the following structure:

E-R$^1$

E meaning a subsequently illustrated radical, E being bonded to R$^1$ via the oxygen atom,

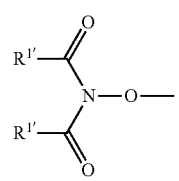

R$^1$ being defined as above and

R$^{1'}$ upon each occurrence, being the same or different and representing hydrogen, a linear or branched alkyl radical, a linear or branched alkylene radical, an aromatic radical, a heteroaromatic radical, or in the case of radicals R$^{1'}$ being bonded to form a ring, the ring being able to be saturated or unsaturated, substituted or unsubstituted and/or at least one or both radicals R$^{1'}$, or the radicals R$^{1'}$ bonded to form a ring, comprising at least one further structural element of the above-illustrated formula I.

In particular, the phosphorus-containing organic oxyimide has one of the subsequent formulae:

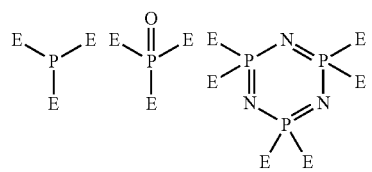

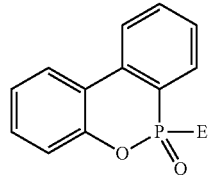

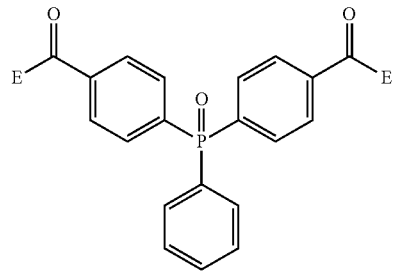

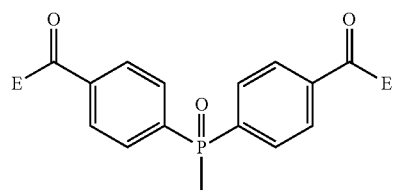

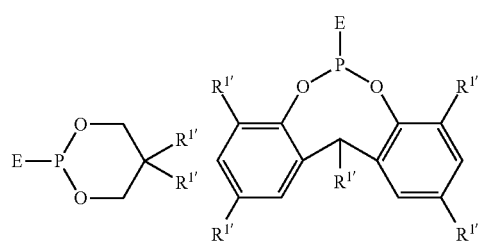

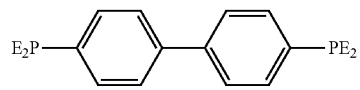

E and R$^{1'}$ having the definition indicated further back.

Organic phosphorus-containing oxyimides which are particularly preferred and to be used by way of example are subsequently illustrated:

According to a first preferred embodiment, the phosphorus-containing organic oxyimide comprises a structural element of the general formula I and has one of the subsequent formulae

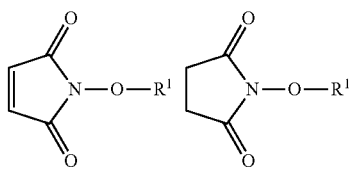

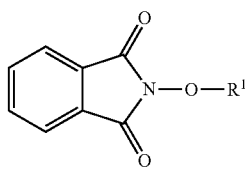

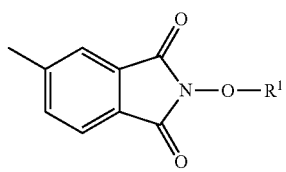

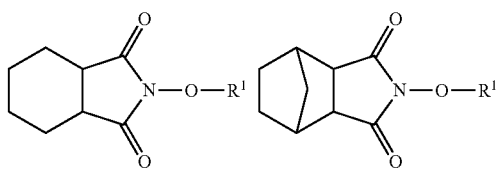

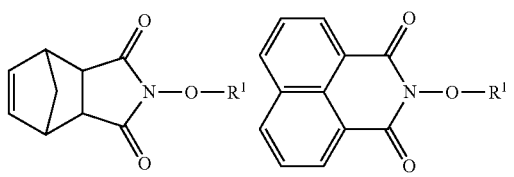

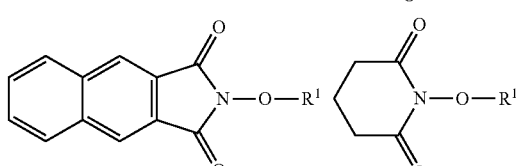

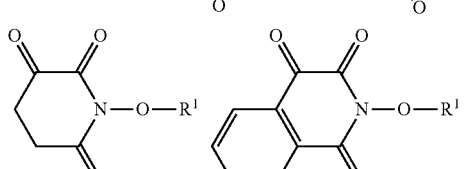

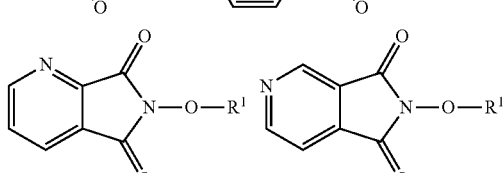

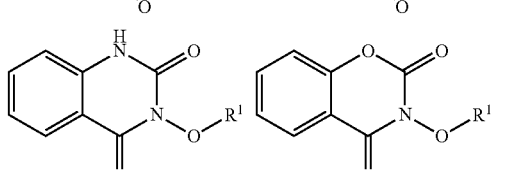

A further preferred embodiment of a phosphorus-containing organic oxyimide according to the invention has two structural elements of the general formula I and has one of the subsequently illustrated formulae

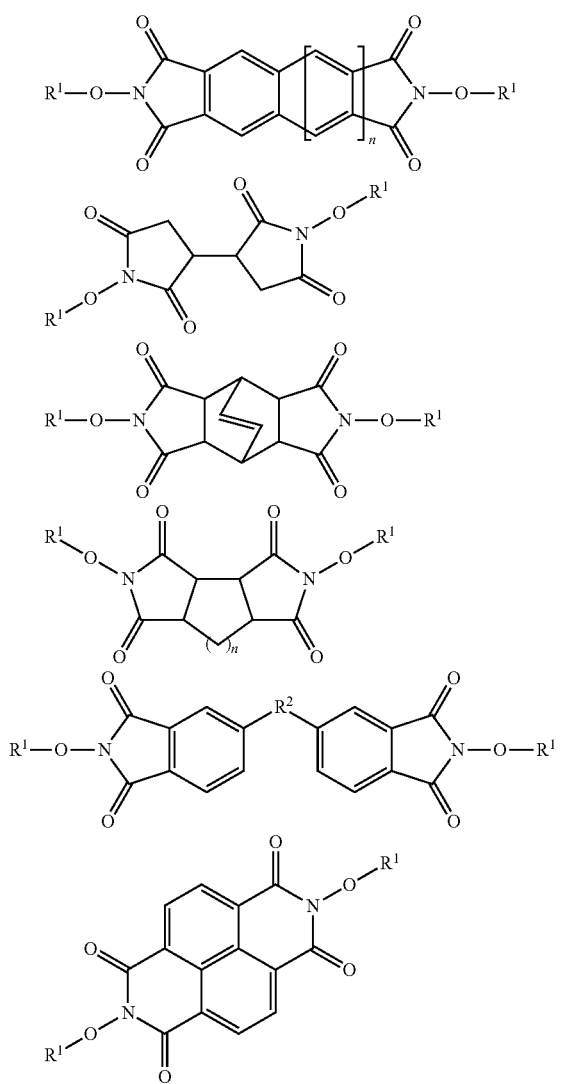

In the case of both previously mentioned embodiments, there thereby applies:

n means 0, 1, 2, 3 or 4, and

R² is selected from the group consisting of possibly substituted alkylene-, cycloalkylene-, arylene-, heteroarylene- or bridging acyl radicals.

A further preferred embodiment provides that the phosphorus-containing organic oxyimide comprises three structural elements of the general formula I and has the subsequent formula

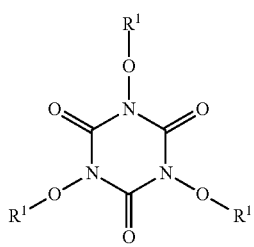

The definition of the radical R¹ is thereby identical to the above-indicated definition.

In the previously indicated formulae, the radical R² is thereby preferably defined as follows: R² is thereby selected preferably from radicals of the group consisting of —(CH$_2$)$_n$— with n=1 to 18, —CH(CH$_3$)—, —C(CH$_3$)$_2$—, —CH(CF$_3$)—, —C(CH$_3$)$_2$—, —O—, —S—, —SO$_2$—, —NHCO—, —CO—, —O—C(O)O— and also the subsequently illustrated groups

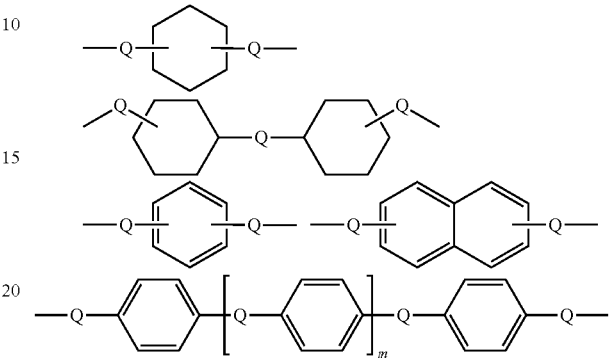

the cycloaliphatic or aromatic ring systems contained in the previously illustrated groups being unsubstituted or substituted by one or more alkyl- and/or alkoxy groups, Q upon each occurrence, being the same or different and being selected from the group consisting of a chemical bond and also the radicals —(CH$_2$)$_n$— with n=1 to 18, —CH(CH$_3$)—, —C(CH$_3$)$_2$—, —CH(CF$_3$)—, —C(CF$_3$)$_2$—, —O—; —S—, —SO$_2$—, —NHCO—, —CO—, —O—C(O)—O, and m being 0 or 1 to 3.

For particular preference, the radicals R² are thereby reproduced by the subsequently illustrated structural elements, Q having the above-indicated meaning:

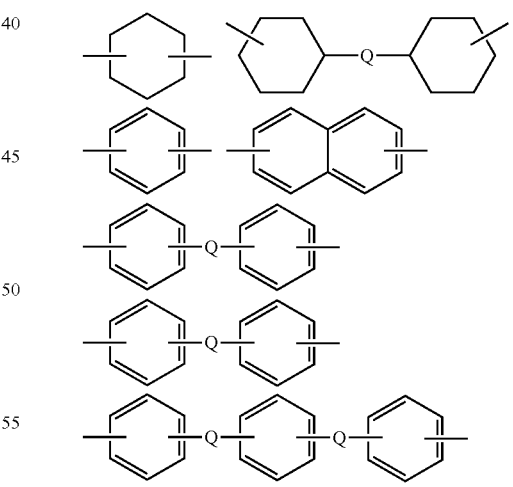

In particular the radicals R² can thereby be given by the subsequent structural elements:

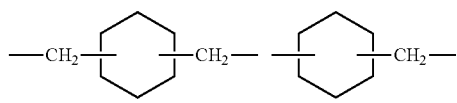

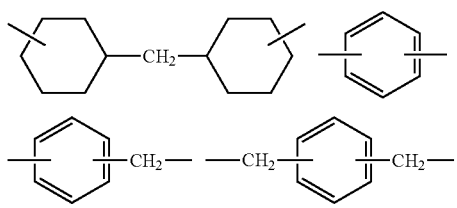
Particularly preferred phosphorus-containing organic oxyimides are thereby selected from the group consisting of the subsequently illustrated compounds:
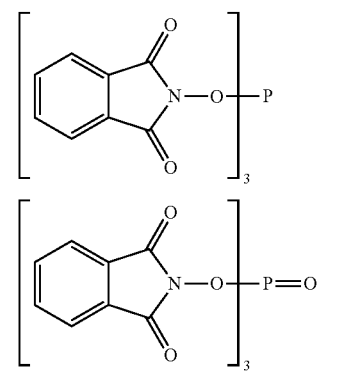
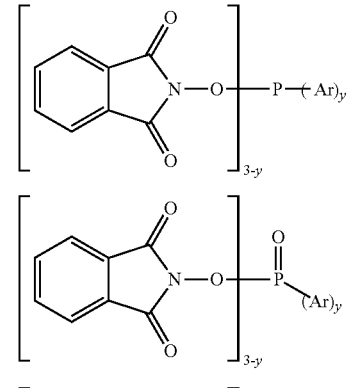
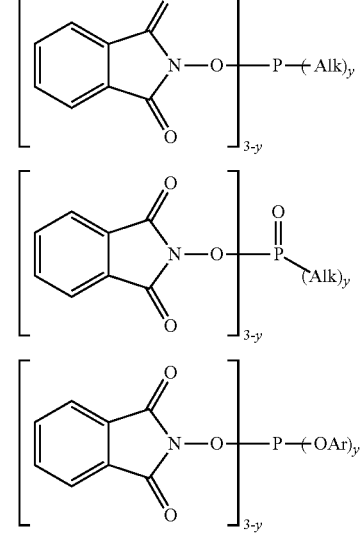
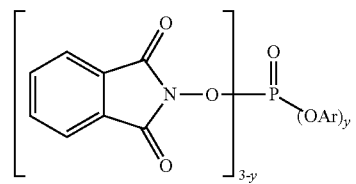
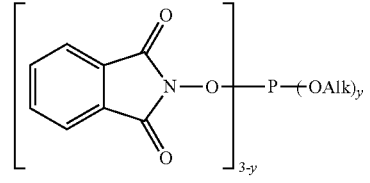
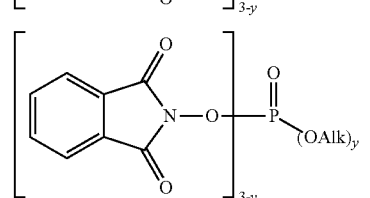
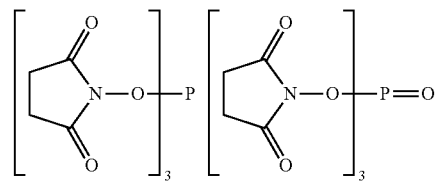
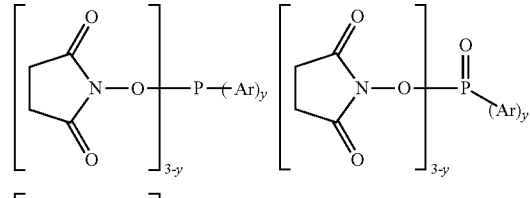
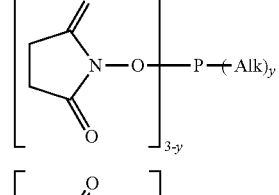
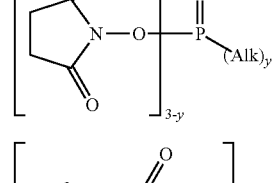
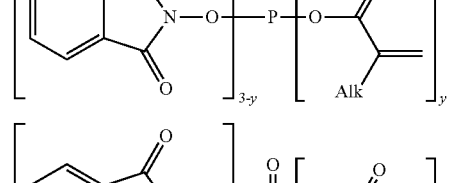
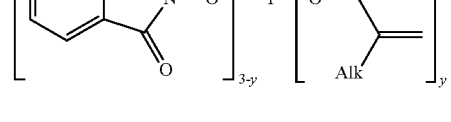

-continued
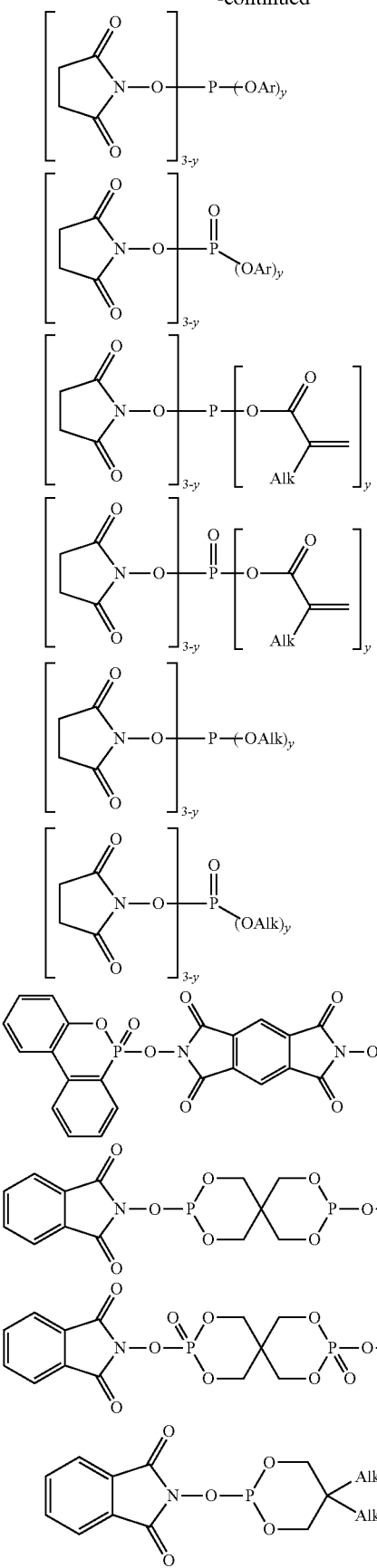
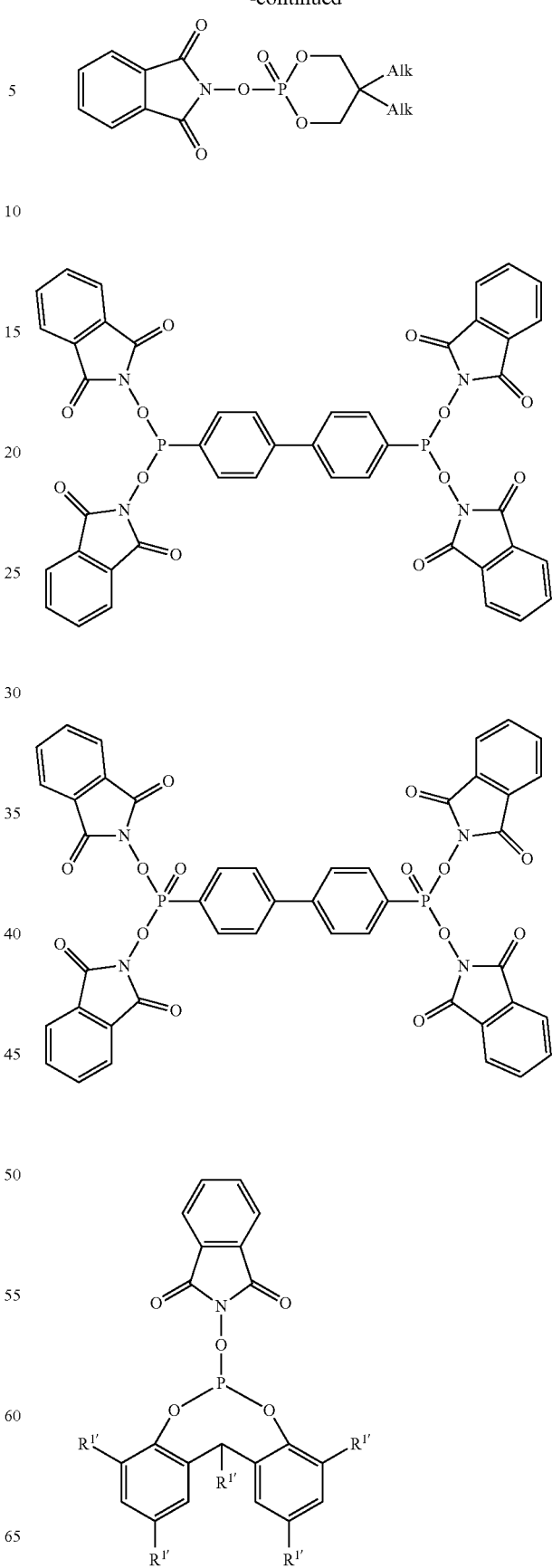

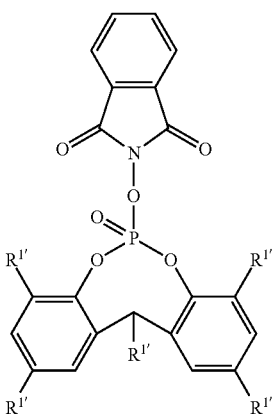

y being 1 or 2

Alk meaning a linear or branched, substituted or unsubstituted alkyl radical, and Ar meaning a substituted or unsubstituted aryl radical or heteroaryl radical.

Likewise it is possible that the phosphorus-containing organic oxyimide is present in the form of a polymer or of a copolymer. The polymer is thereby constructed from the subsequently indicated repetition units, the copolymer comprises at least one of the subsequently indicated repetition units:

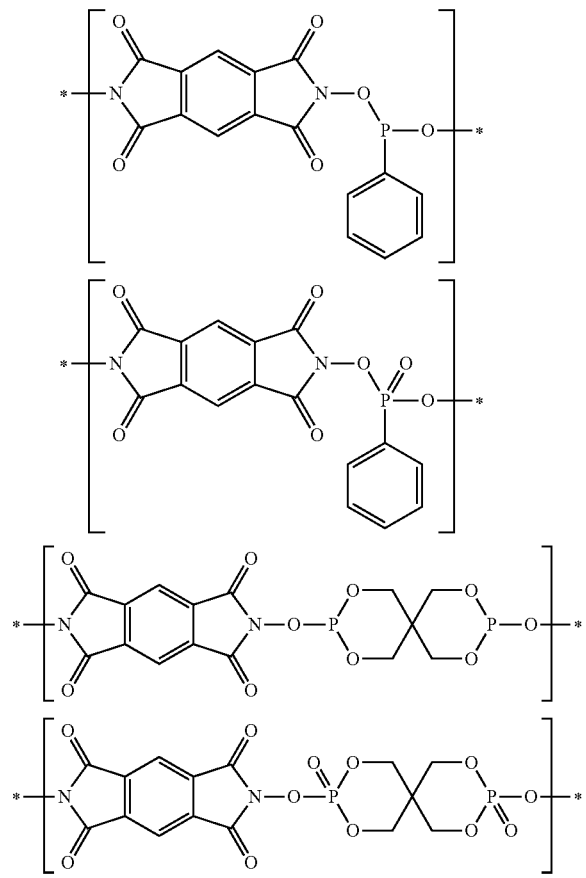

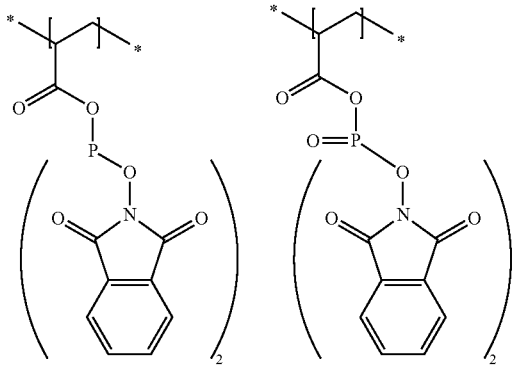

The plastic materials are thereby preferably thermoplastic polymers, selected in particular from the group consisting of
a) polymers made of olefins or diolefins, such as e.g. polyethylene (LDPE, LLDPE, VLDPE, ULDPE, MDPE, HDPE, UHMWPE), metallocene-PE (m-PE), polypropylene, polyisobutylene, poly-4-methylpentene-1, polybutadiene, polyisoprene, polycyclooctene, polyalkylene-carbon monoxide copolymers and also copolymers in the form of statistical or block structures, such as e.g. polypropylene-polyethylene (EP), EPM or EPDM, ethylene-vinyl acetate (EVA), ethylene-acrylester, such as e.g. ethylene-butylacrylate, ethylene-acrylic acid and the salts thereof (ionomers), and also terpolymers, such as e.g. ethylene-acrylic acid-glycidylacrylate, graft polymers, such as e.g. polypropylene-graft-maleic anhydride, polypropylene-graft-acrylic acid, polyethylene-graft-acrylic acid, polyethylene-polybutylacrylate-graft-maleic anhydride,
b) polystyrene, polymethylstyrene, polyvinylnaphthalene, styrene-butadiene (SB), styrene-butadiene-styrene (SBS), styrene-ethylene-butylene-styrene (SEBS), styrene-ethylene-propylene-styrene, styrene-isoprene, styrene-isoprene-styrene (SIS), styrene-butadiene-acrylonitrile (ABS), styrene-acrylonitrile-acrylate (ASA), styrene-ethylene, styrene-maleic anhydride polymers including corresponding graft copolymers, such as e.g. styrene on butadiene, maleic anhydride on SBS or SEBS, and also graft copolymers made of methylmethacrylate, styrene-butadiene and ABS (MABS),
c) halogen-containing polymers, such as e.g. polyvinyl chloride (PVC), polychloroprene and polyvinylidene chloride (PVDC), copolymers made of vinyl chloride and vinylidene chloride, or made of vinyl chloride and vinyl acetate, chlorinated polyethylene, polyvinylidene fluoride,
d) polymers of unsaturated esters, such as e.g. polyacrylates and polymethacrylates, such as polymethylmethacrylate (PMMA), polybutylacrylate, polylaurylacrylate, polystearylacrylate, polyglycidylacrylate, polyglycidylmethacrylate, polyacrylonitrile, polyacrylamides, copolymers, such as e.g. polyacrylonitrile-polyalkylacrylate, polymethacrylimide,
e) polymers made of unsaturated alcohols and derivatives, such as e.g. polyvinyl alcohol, polyvinyl acetate, polyvinyl butyral,
f) polyacetals, such as e.g. polyoxymethylene (POM) or copolymers, with e.g. butanal,
g) polyphenylene oxides and blends with polystyrene or polyamides, h) polymers of cyclic ethers, such as e.g. polyethylene glycol, polypropylene glycol, polyethylene oxide, polypropylene oxide, polytetrahydrofuran, i) polyurethanes made of hydroxy-terminated polyethers or polyesters and aromatic or aliphatic isocyanates, in particular linear polyurethanes, polyureas, j) polyamides, such as e.g. polyamide-6, 6.6, 6.10, 4.6, 4.10, 6.12, 12.12, polyamide 11, polyamide 12 and also (partially) aromatic polyamides, such as e.g. polyphthalamides, e.g. produced from terephthalic acid and/or isophthalic acid and aliphatic diamines or from aliphatic dicarboxylic acids, such as e.g. adipic acid or sebacic acid, and aromatic diamines, such as e.g. 1,4- or 1,3-diaminobenzene, blends of different polyamides, such as e.g. PA-6 and PA 6.6 or blends of polyamides and polyolefins, such as e.g. PA/PP, k) polyimides, polyamideimides, polyetherimides, polyesterimides, poly(ether)ketones, polysulphones, polyethersulphones, polyarylsulphones, polyphenylene sulphide, polybenzimidazoles, polyhydantoins, l) polyesters made of aliphatic or aromatic dicarboxylic acids and diols or made of hydroxycarboxylic acids, such as e.g. polyethylene terephthalate (PET), polybutylene terephthalate (PBT), polypropylene terephthalate, polyethylene naphthylate, poly-1,4-dimethylolcyclohexane terephthalate, polyhydroxybenzoate, polyhydroxynaphthalate, polylactic acid (PLA), polyhydroxybutyrate (PHB), polyhydroxyvalerate (PVH), m) polycarbonates, polyester carbonates and also blends, such as e.g. PC/ABS, PC/PBT, PC/PET/PBT, PC/PA, n) cellulose derivatives, such as e.g. cellulose nitrate, cellulose acetate, cellulose propionate, cellulose butyrate, o) duromeric or elastomeric, non-thermoplastic plastic materials, p) and also mixtures, combinations or blends of two or more of the previously mentioned polymers.

Provided the polymers indicated under a) to o) concern copolymers, these can be present in the form of statistical ("random"), block- or "tapered" structures.

Provided the polymers indicated under a) to o) concern stereoregular polymers, these can be present in the form of isotactic, stereotactic but also atactic forms or as stereoblock copolymers.

Furthermore, the polymers indicated under a) to o) can have both amorphous and (partially) crystalline morphologies.

Possibly, the polyolefins mentioned under a) can also be present crosslinked, e.g. crosslinked polyethylene, which is then termed X-PE.

The mentioned polymers a) to o) can thereby be present not only as virgin material but also in the form of recyclates, e.g. as production waste or "post-consumer" recyclates.

The flame retardants according to the invention can be used in particular in the following duromeric or elastomeric, non-thermoplastic plastic materials:

a) epoxy resins, consisting of di- or polyfunctional epoxy compounds in combination with e.g. hardeners, based on amines, anhydrides, dicyanodiamides, mercaptans, isocyanates or catalytically acting hardeners, b) phenol resins, such as e.g. phenol-formaldehyde resins, urea-formaldehyde resins, melamine-formaldehyde resins, c) unsaturated polyester resins made of unsaturated dicarboxylic acids and diols, d) silicones, e) polyurethanes as reaction products made of di- or polyfunctional isocyanates and polyols, polyureas, f) alkyd resins, allyl resins.

For very particular preference, the flame retardants according to the invention are used in the case of polyolefins, preferably polypropylene and/or polyethylene and the copolymers and blends thereof.

Furthermore it is preferred if the at least one phosphorus-containing organic oxyimide is used in combination with at least one further flame retardant, selected from the group consisting of a) inorganic flame retardants, such as e.g. Al(OH)$_3$, Mg(OH)$_2$, AlO(OH), MgCO$_3$, layer silicates, such as e.g. montmorillonite or sepiolite, non- or organically modified, double salts, such as e.g. Mg—Al silicates, POSS (Polyhedral Oligomeric Silsesquioxane) compounds, huntite, hydromagnesite or halloysite and also Sb$_2$O$_3$, Sb$_2$O$_5$, MoO$_3$, zinc stannate, zinc hydroxystannate, b) nitrogen-containing flame retardants, such as e.g. melamine, melem, melam, melon, melamine derivatives, melamine condensation products or melamine salts, benzoguanamine, polyisocyanurates, allantoin, (poly)phosphacenes, in particular melamine cyanurate, melamine phosphate, dimelamine phosphate, melamine pyrophosphate, melamine polyphosphate, melamine-methane phosphonate, melamine-metal phosphates, such as e.g. melamine aluminium phosphate, melamine zinc phosphate, melamine magnesium phosphate, and also the corresponding pyrophosphates and polyphosphates, poly-[2,4-(piperazin-1,4,-yl]-6-(morpholin-4-yl)1,3,5-triazine], ammonium polyphosphate, melamine borate, melamine hydrobromide, ethylene diamine methane phosphonate, c) radical formers, such as e.g. alkoxyamines, hydroxylamine esters, azo compounds, dicumyl or polycumyl, non-phosphorus-containing hydroxyimides or the derivatives thereof, such as e.g. hydroxyimide ester or hydroxyimide ether, d) phosphorus-containing flame retardants, such as e.g. inorganic or organic phosphonates, such as e.g. aluminium phosphonate, phosphonate ester, oligomeric and polymeric derivatives of methane phosphonic acid, red phosphorus, phosphates, such as e.g. resorcin diphosphate, bisphenol-A-diphosphate and the oligomers thereof, triphenylphosphate, ethylene diamine phosphate, phosphinates, such as e.g. salts of hypophosphorous acid and the derivatives thereof, such as alkyl phosphinate salts, e.g. diethylphosphinate aluminium or diethylphosphinate zinc or aluminium phosphinate, aluminium phosphite, aluminium phosphate, 9,10-dihydro-9-oxa-10-phosphorylphenanthrene-10-oxide (DOPO) and the substituted compounds thereof, e) halogen-containing flame retardants based on chlorine and bromine, such as e.g. polybrominated diphenyl oxides, such as e.g. decabromodiphenyl oxide, tris(3-bromo-2,2-bis(bromomethyl)propylphosphate, tris(tribromoneopentyl)phosphate, tetrabromophthalic acid, 1,2-bis(tribromophenoxy)ethane, hexabromocyclododecane, brominated diphenylethane, tris-(2,3,-dibromopropyl)isocyanurate, tetrabromobisphenol-A-bis(2,3)dibromopropylether), ethylenebis(tetrabromophthalimide), tetrabromo-bisphenol A, brominated polystyrene, brominated polybutadiene or polystyrene-brominated polybutadiene copolymers, brominated epoxy resin, polypentabromobenzylacrylate, brominated polyphenylene ether, possibly in combination with Sb$_2$O$_3$ and/or Sb$_2$O$_5$, f) borates, such as e.g. zinc borate or calcium borate, possibly on silica as carrier material, g) sulphur-containing compounds, such as e.g. elementary sulphur, disulphides and polysulphides, thiuram sulphide, dithiocarbamates, mercaptobenzothiazole and sulphenamides, h) antidrip agents, such as e.g. polytetrafluoroethylene, i) silicon-containing compounds, such as e.g. polyphenylsiloxanes, j) carbon modifications, such as e.g. carbon nanotubes (CNT) or graphene, and also combinations or mixtures hereof.

The halogen-containing flame retardants mentioned under e) frequently concern commercial products which are commercially available, e.g. from the companies Albemarle, Chemtura/Great Lakes or ICL-IP.

In particular in the case of combinations of the compounds used according to the invention according to formulae I to IV with at least one radical former as further flame retardant, synergistic effects result.

Radical formers in the sense of the present invention are compounds which can produce radicals by means of thermal and light-induced cleavage. Suitable radical formers for the applications present here are those which have sufficient thermal stability for the plastic material- or coating-processing processes, i.e. during processing, still form no or only very small quantities of radicals and produce radicals spontaneously only at higher temperatures, such as occur only in the case of fire. The respective processing processes and temperatures for coatings and plastic material processing processes are known to the person skilled in the art. Plastic material processing processes and associated temperatures can however also be obtained from the expert literature, such as e.g. H. Domininghaus, P. Elsner, P. Eyerer, T. Hirth, Kunststoffe (Plastic materials), 8$^{th}$ edition, Springer 2012.

The radical former is thereby selected preferably from the group consisting of N-alkoxyamines, —C—C— radical formers, radical formers with azo groups (—N=N—), radical formers with hydrazine groups (—NH—HN—), radical formers with hydrazone groups (>C=N—NH—), radical formers with azine groups (>C=N—N=C<), radical formers with triazene groups (—N=N—N<) or from iminoxytriazines.

The production of suitable azo compounds is described for example in M. Aubert et al. Macromol. Sci. Eng. 2007, 292, 707-714 or in WO 2008101845, the production of hydrazones and azines in M. Aubert et al., Pol. Adv. Technol. 2011, 22, 1529-1538, the production of triazenes in W. Pawelec et al., Pol. Degr. Stab. 2012, 97, 948-954. The synthesis of iminoxytriazines is described in WO 2014/064064.

In particular, the radical formers to be used are thereby selected from the group consisting of a) N-alkoxyamines according to the subsequently illustrated structural formula,

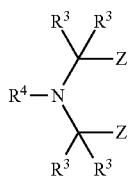

$R^3$ standing for hydrogen or a possibly substituted alkyl-, cycloalkyl-, aryl-, heteroaryl- or acyl radical, in particular being a C1 to C4 alkyl radical, $R^4$ standing for an alkoxy-, aryloxy-, cycloalkoxy-, aralkoxy- or acyloxy radical, Z standing for hydrogen or a possibly substituted alkyl-, cycloalkyl-, aryl-, heteroaryl- or acyl radical, the two radicals Z also being able to form a closed ring which can be substituted possibly by ester-, ether-, amine-, amide-, carboxy- or urethane groups, E stands for an alkoxy-, aryloxy-, cycloalkyloxy-, aralkoxy- or acyloxy radical, b) azo compounds according to the subsequently illustrated structural formulae,

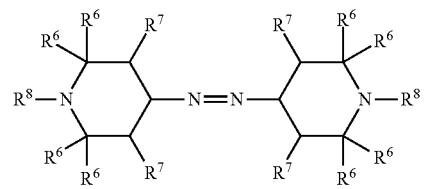

$R^5$ meaning an alkyl-, cycloalkyl- or aryl radical, $R^6$ upon each occurrence, being the same or different and meaning a linear or branched alkyl radical, $R^7$ upon each occurrence, being the same or different and meaning hydrogen or a linear or branched alkyl radical, and $R^8$ upon each occurrence, being the same or different and meaning an alkyl-, alkoxy-, aryloxy-, cycloalkyloxy-, aralkoxy- or acyloxy radical, c) dicumyl according to the subsequently illustrated structural formula

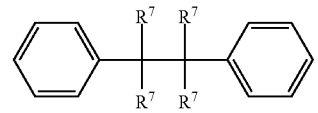

$R^7$ having the previously indicated meaning, preferably being methyl, d) and/or polycumyl according to the subsequently illustrated structural formula

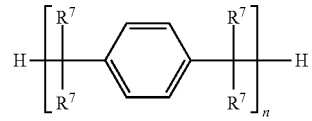

$R^7$ having the previously indicated meaning, preferably being methyl, and $2<n<100$.

Typical examples of the previously mentioned N-alkoxyamines of the indicated structure are thereby: 1-cyclohexyloxy-2,2,6,6-tetramethyl-4-octadecylaminopiperidine; bis(1-octyloxy-2,2,6,6-tetramethylpiperidin-4-yl) sebacate; 2,4-bis[(1-cyclohexyloxy-2,2,6,6-tetramethylpiperidin-4-yl)butylamino]-6-(2-hydroxyethylamino-S-triazine; bis(1-cyclohexyloxy-2,2,6,6-tetramethylpiperidin-4-yl) adipate; 2,4-bis[(1-cyclohexyloxy-2,2,6,6-tetramethylpiperidin-4-yl)butylamino]-6-chloro-S-triazine; 1-(2-hydroxy-2-methylpropoxy)-4-hydroxy-2,2,6,6-tetramethylpiperidine; 1-(2-hydroxy-2-methylpropoxy)-4-oxo-2,2, 6,6-tetramethylpiperidine; 1-(2-hydroxy-2-methylpropoxy)-4-octadecanoyloxy-2,2,6,6-tetramethylpiperidine; bis(1-(2-hydroxy-2-methylpropoxy)-2,2,6,6-tetramethylpiperidin-4-yl)sebacate; bis(1-(2-hydroxy-2-methylpropoxy)-2,2,6,6-tetramethylpiperidin-4-yl)adipate; 2,4-bis{N-[1-(2-hydroxy-2-methylpropoxy)-2,2,6,6-tetramethylpiperidin-4-yl]-N-butylamino}-6-(2-hydroxyethylamino)-S-triazine); 4-piperidinol, 2,2,6,6-tetramethyl-1-(undecyloxy)-,4,4'-carbonate; the reaction product of 2,4-bis[(1-cyclohexyloxy-2,2,6,6-tetramethylpiperidin-4-yl)butylamino]-6-chloro-S-triazine with N,N'-bis(3-aminopropylethylenediamine); the oligomer compound, which is the condensation product of 4,4'-hexamethylene-bis(amino-2,2,6,6-tetramethylpiperidine) and 2,4-dichloro-6-[(1-cyclohexyloxy-2,2,6,6-tetramethyl-4-yl)butylamino]-S-triazine, closed at the ends with 2-chloro-4,6-bis(dibutylamino)-S-triazine; aliphatic hydroxylamine, such as e.g. distearyl hydroxylamine; and also compounds of the formulae The above-mentioned compounds are partially commercial products and are sold under the following trade names: FLAMESTAB NOR 116®, TINUVIN NOR 371®, IRGATEC CR 76® by BASF SE, Hostavin NOW® by Clariant or ADK Stab LA 81® by Adeka. Dicumyl and polycumyl are commercial products which are obtainable for example from United Initiators.

The at least one further flame retardant can be in particular also a phosphorus-containing flame retardant. Preferred phosphorus-containing flame retardants are thereby phosphinates of the following structures:

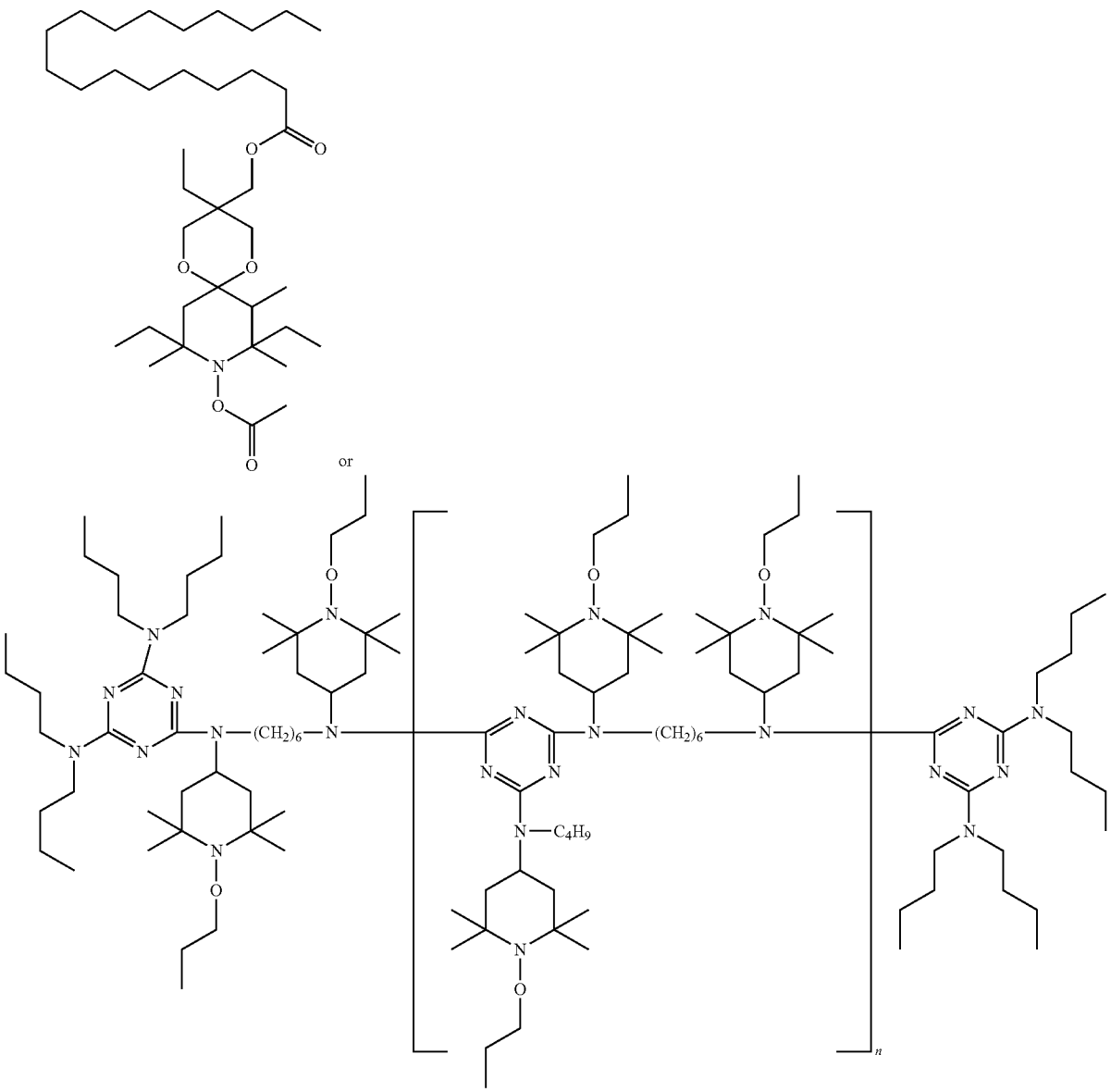

in which n=1-15.

R[1] and R[2] preferably being identical or different and being selected from linear or branched C1-C6 alkyl and/or aryl; M being selected from the group consisting of Mg, Ca, Al, Sb, Sn, Ge, Ti, Fe, Zr, Ce, Bi, Sr, Mn, Li, Na, K, Zn and/or a protonated nitrogen base, preferably calcium ions, magnesium ions, aluminium ions and/or zinc ions; and m=1-4, preferably 2 or 3; n=1-4, preferably 1 or 3; x=1-4, preferably 1 or 2. In a particularly preferred embodiment, $R_1$=alkyl, $R_2$=alkyl and M=Al or Zn.

A particularly preferred example of a phosphinate according to the invention are the commercially available products Exolit OP® by Clariant SE.

Further preferred phosphorus-containing flame retardants are metal salts of hypophosphorous acid with a structure according to the formula

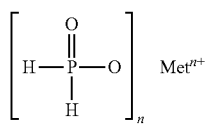

Met being a metal, selected from groups I, II, III and IV of the periodic table of elements, and n being a number from 1 to 4 which corresponds to the charge of the corresponding metal ion Met. $Met^{n+}$ is for example $Na^+$, $Ca^{2+}$, $Mg^{2+}$, $Zn^{2+}$, $Ti^{4+}$ or $Al^{3+}$, wherein $Ca^{2+}$, $Zn^{2+}$ and $Al^{3+}$ are particularly preferred.

The above-mentioned salts of hypophosphorous acid are partially commercially available, e.g. with the title Phoslite® by Italmatch Chemicals.

A further preferred group of phosphorus-containing flame retardants are phosphonates or phosphonic acid diaryl esters of a structure according to the following formula:

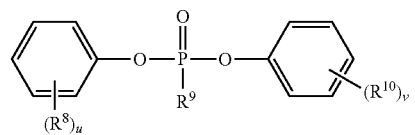

$R_8$ and $R_{10}$=H, alkyl, preferably C1-C4 alkyl, $R_9$=C1-C4 alkyl, u=1-5 and v=1-5.

Corresponding structures can also be present in the form of phosphonate oligomers, polymers and copolymers. Linear or branched phosphonate oligomers and polymers are known from the state of the art. For branched phosphonate oligomers and polymers, reference is made to the U.S. Pat. Nos. 2,716,101, 3,326,852, 4,328,174, 4,331,614, 4,374,971, 4,415,719, 5,216,113, 5,334,692, 3,442,854, 6,291,630 B1, 6,861,499 B2 and 7,816,486 B2. For phosphonate oligomers, reference is made to the US patent applications US 2005/0020800 A1, US 2007/0219295 A1 and US 2008/0045673 A1. With respect to linear phosphonate oligomers and polymers, reference is made to the US patent documents U.S. Pat. Nos. 3,946,093, 3,919,363, 6,288,210 B1, 2,682,522 and 2,891,915.

Oligomeric and polymeric phosphonates are available for example under the trade name Nofia® by FRX Polymers.

A further preferred group of phosphorus-containing flame retardants are compounds based on oxaphosphorin oxide and the derivatives thereof with for example the following structures:

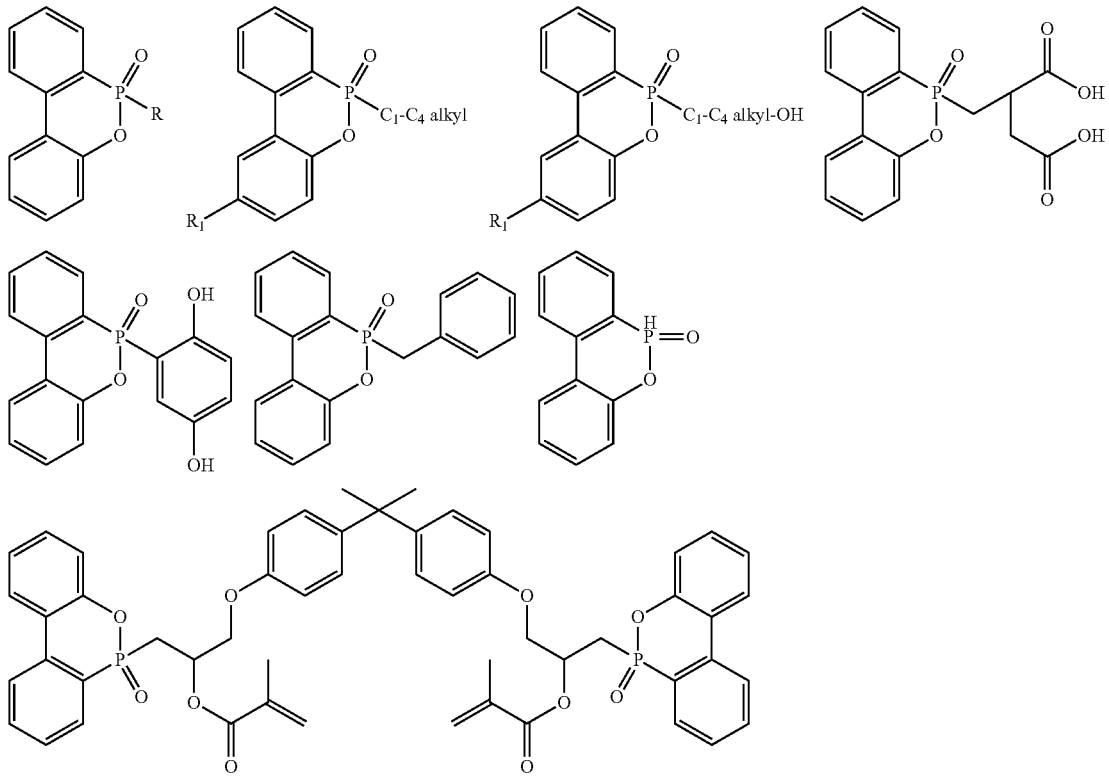

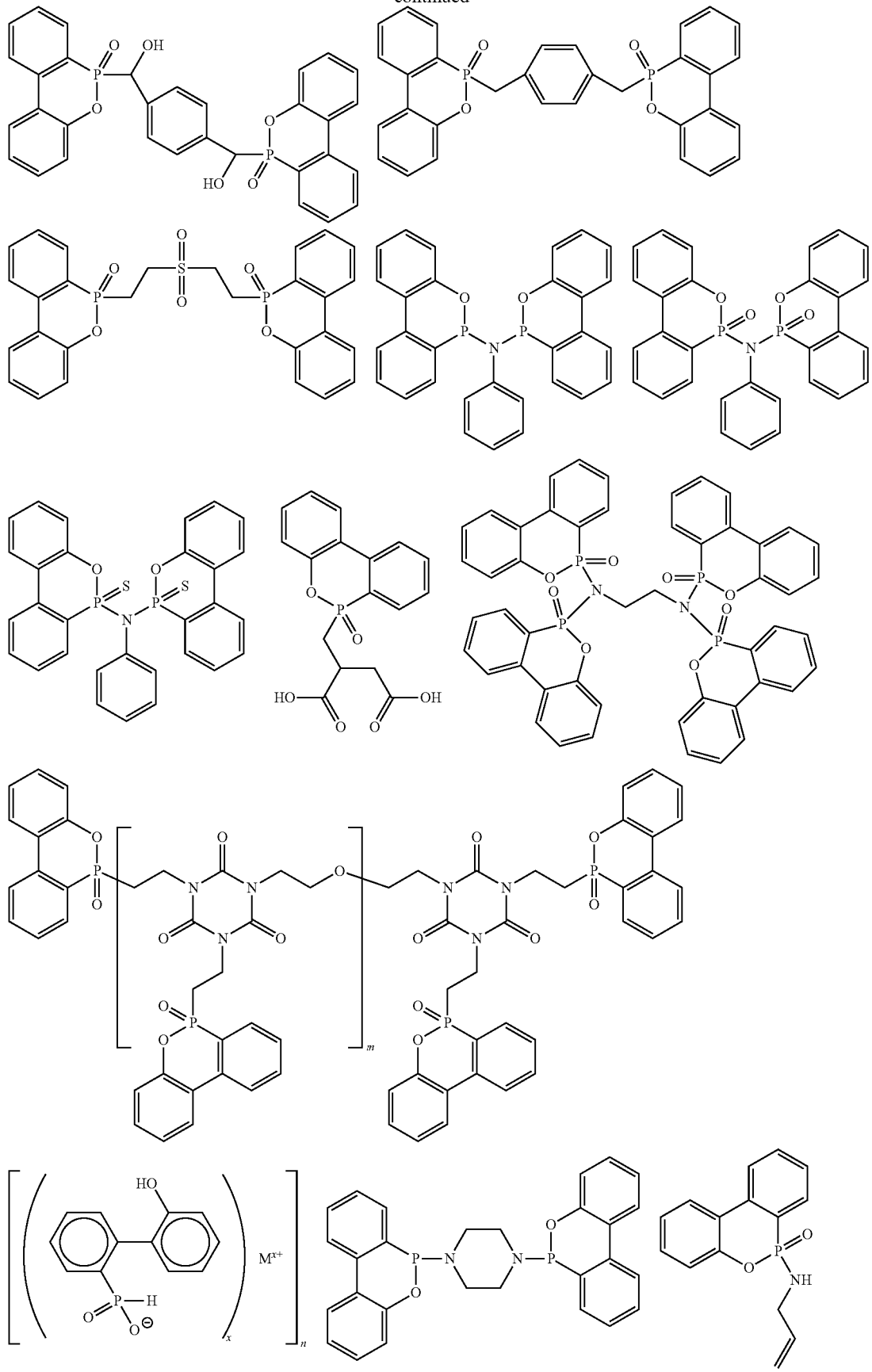

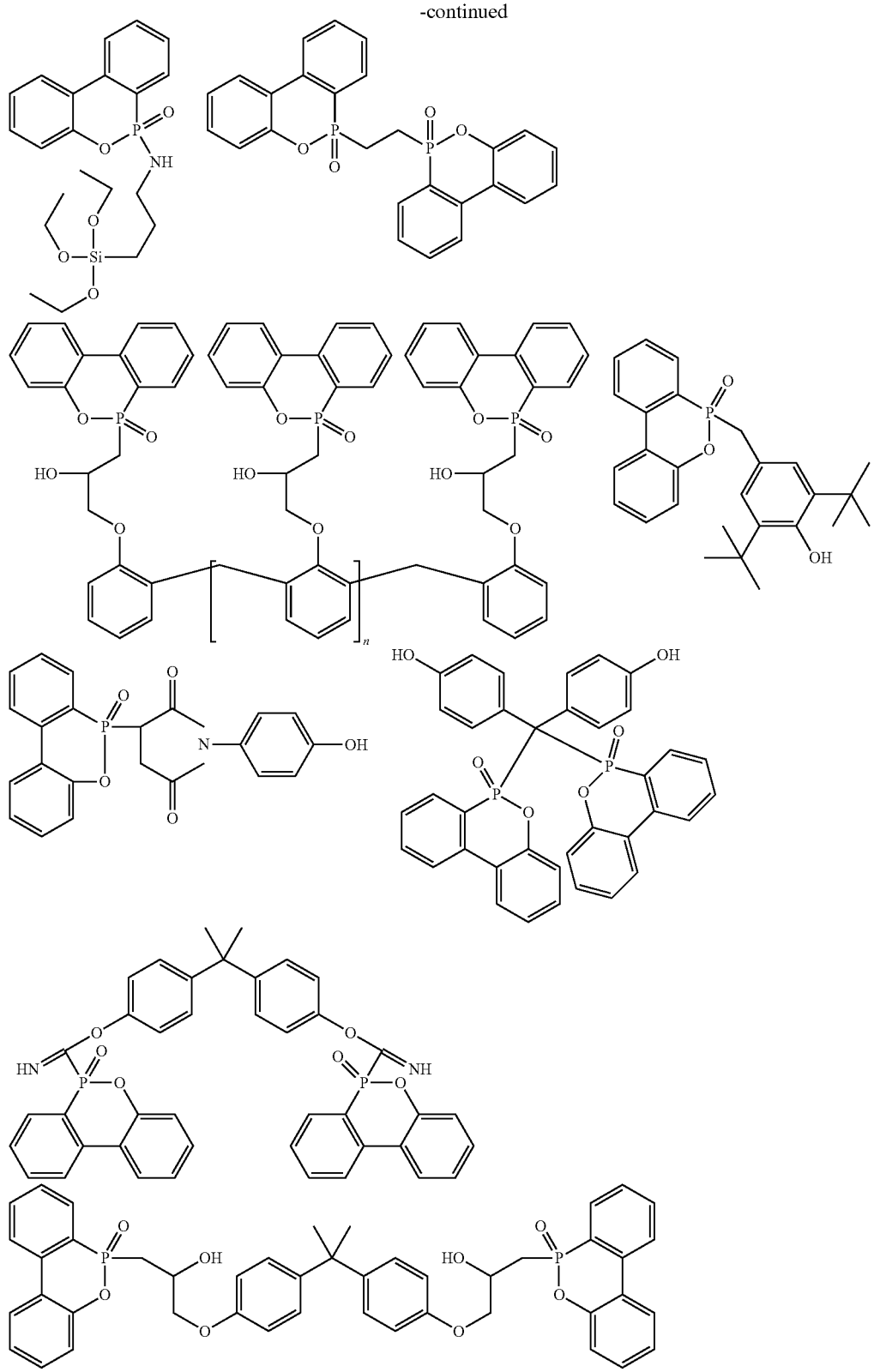

M being a metal, selected from the second, third, twelfth or thirteenth group of the periodic table of elements, x=2 or 3, n≥10, m=0-25, R=H, halogen or an aliphatic or aromatic radical with 1-32 C atoms and $R_1$=H, C1-C6 alkyl.

Products based on oxaphosphorin oxide are marketed for example under the trade name Ukanol® by Schill and Seilacher GmbH. Further compounds can be produced for example according to the patent specifications WO 2013020696, WO 2010135398, WO 03070736, WO 2006084488, WO 2006084489, WO 2011000019, WO 2013068437, WO 2013072295.

Further synergistic phosphorus-containing flame retardants are cyclic phosphonates of a structure according to one of the following formulae:

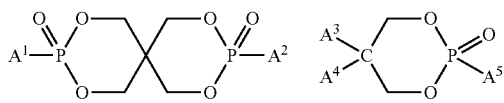

$A^1$ and $A^2$, independently of each other, representing a substituted or unsubstituted, straight-chain or branched alkyl group with 1 to 4 carbon atoms, substituted or unsubstituted benzyl, substituted or unsubstituted phenyl, substituted or unsubstituted naphthyl, and $A^3$ and $A^4$, independently of each other, being methyl or ethyl and $A^5$ being a straight-chain or branched alkyl group with 1 to 4 carbon atoms or a phenyl- or benzyl group which can have respectively up to 3 methyl groups.

Cyclic phosphonates are marketed for example by the company Thor GmbH under the trade name Aflammit® or can be produced according to EP 2450401.

Further synergistic phosphorus-containing flame retardants are phosphacenes, in particular polymeric phosphacenes. A corresponding product is available commercially, e.g. under the title SPB-100 by Otsuka Chemicals.

The at least one further flame retardant can be in particular also a nitrogen-containing flame retardant. Preferred nitrogen-containing flame retardants are melamine polyphosphate, melamine cyanurate, melamine-metal phosphates, poly-[2,4-(piperazin-1,4-yl)-6-(morpholin-4-yl)-1,3,5-triazine] and ammonium polyphosphate. These compounds are commercial products and available under the trade names Melapur® by BASF SE, Budit® by Budenheim Chemische Fabrik, Exolit® by Clariant, Safire® by Huber Chemicals or MCA PPM Triazine by MCA Technologies GmbH.

The combination of the phosphorus-containing organic oxyimides according to the invention with a phosphonate and/or a (poly)phosphacene is very particularly preferred.

Preferably, the phosphorus-containing organic oxyimides and the at least one further flame retardant are used in a weight ratio of 99:1 to 1:99, preferably of 5:95 to 50:50, particularly preferably of 10:90 to 30:70.

It is likewise possible and preferred that the previously mentioned phosphorus-containing organic oxyimides are used in combination with at least one phosphorus-containing compound. The phosphorus-containing compound is thereby not identical to the previously mentioned phosphorus-containing flame retardants. These phosphorus-containing compounds can thereby be selected in particular from the group consisting of organic phosphites or phosphonites. Suitable compounds are then for example: triphenylphosphite, diphenylalkylphosphites, phenyldialkylphosphites, tri(nonylphenyl)phosphite, trilaurylphosphites, trioctadecylphosphite, distearylpentaerythritoldiphosphite, tris-(2,4-di-tert-butylphenyl)phosphite, diisodecylpentaerythritoldiphosphite, bis(2,4-di-tert-butylphenyl)pentaerythritoldiphosphite, bis(2,4-di-cumylphenyl)pentaerythritoldiphosphite, bis(2,6-di-tert-butyl-4-methylphenyl)pentaerythritoldiphosphite, diisodecyloxypentaerythritoldiphosphite, bis(2,4-di-tert-butyl-6-methylphenyl)pentaerythritoldiphosphite, bis(2,4,6-tris(tert-butylphenyl)pentaerythritoldiphosphite, tristearylsorbitoltriphosphite, tetrakis(2,4-di-tert-butylphenyl)-4,4'-biphenylenediphosphonite, 6-isooctyloxy-2,4,8,10-tetra-tert-butyl-12H-dibenzo[d,g]-1,3,2-dioxaphosphocine, bis(2,4-di-tert-butyl-6-methylphenyl)methylphosphite, bis(2,4-di-tert-butyl-6-methylphenyl)ethylphosphite, 6-fluoro-2,4,8,10-tetra-tert-butyl-12-methyldibenzo[d,g]-1,3,2-dioxaphosphocine, 2,2'2''-nitrilo[triethyltris(3,3'',5,5'-tetra-tert-butyl-1,1'-biphenyl-2,2'-diyl)phosphite], 2-ethylhexyl (3,3',5,5'-tetra-tert-butyl-1,1'-biphenyl-2,2'-diyl))phosphite, 5-butyl-5-ethyl-2-(2,4,6-tri-tert-butylphenoxy)-1,3,2-dioxaphosphirane.

In addition, it is advantageous if the phosphorus-containing organic oxyimides, relative to the plastic materials, are used at 0.01 to 30% by weight, preferably at 0.1 to 20% by weight, particularly preferably at 1 to 10% by weight.

In addition, the present invention relates to a flame-retardant and/or stabilised, in particular (photo)oxidatively stabilised, plastic material composition, comprising or consisting of:
a) 60 to 99.9 parts by weight, preferably 60 to 98, particularly preferably 70 to 95 parts by weight, of at least one plastic material, in particular of at least one thermoplastic polymer,
b) 0.1 to 40 parts by weight, preferably 1 to 25, particularly preferably 2.5 to 15 parts by weight, of at least one phosphorus-containing organic oxyimide, comprising at least one structural element of the subsequently illustrated formula I,

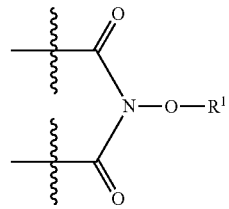

Formula I c) 0 to 25, preferably 1 to 20 parts by weight, particularly preferably 2.5 to 15 parts by weight, of at least one further flame retardant and also
d) 0 to 25 parts by weight, preferably 1 to 20 parts by weight, particularly preferably 2.5 to 15 parts by weight, of at least one phosphorus-containing compound.

The oxyimide salts and/or flame retardants used in the composition correspond to the above-described oxyimide salts or flame retardants. In particular, it is preferred if the flame retardant is a phosphonate or a (poly)phosphacene.

Preferred compositions consist of:
(A) 60-98 parts of at least one thermoplastic polymer
(B) 0.1-20 parts of at least one phosphorus-containing oxyimide
(C) 1-20 parts of a further flame retardant For the purposes of the composition according to the invention, all of the previously-described oxyimides are used.

In particular, the above-described phosphorus-containing organic oxyimides in which at least one, preferably all, phosphorus atoms are present in low oxidation states, i.e. −2, −1, 0, +1, +2, +3, can furthermore be used as stabilisers, e.g. in order to protect a plastic material from oxidation during processing and hence have an antioxidant effect.

Particularly preferred compounds as antioxidants are thereby oxyimides with phosphite or phosphonite groups. By means of stabilisation, (photo)oxidative damage to the plastic material is delayed or prevented. A further subject of the invention is therefore a stabilised plastic material which comprises the above-mentioned phosphorus-containing oxyimides in low oxidation states as stabilisers and also a method for the production of this stabilised plastic material.

With respect to the plastic material, in particular the thermoplastic polymer and also the phosphorus-containing organic oxyimide, reference is thereby made to the definitions and explanations already indicated further back. All of the previously described embodiments apply likewise without restriction to the flame-retardant plastic material composition.

It is thereby further advantageous in the case of the flame-retardant plastic material composition that in addition
  e) up to 40 parts by weight of at least one reinforcing- or filling material and/or
  f) up to 5 parts by weight of at least one additive from the class of phenolic antioxidants, phosphites, acid collectors, hindered amines, dispersants and also combinations hereof
are contained.

The flame-retardant plastic material composition can include additives, selected from the group consisting of UV absorbers, light stabilisers, stabilisers, hydroxylamines, benzofuranones, nucleation agents, impact strength enhancers, plasticisers, lubricants, rheology modifiers, chain lengtheners, processing aids, pigments, colourants, optical brighteners, antimicrobial active substances, antistatic agents, slip agents, antiblocking agents, coupling means, dispersants, compatibilisers, oxygen collectors, acid collectors, marking means or anti-fogging means. In a preferred embodiment, the compositions comprise in particular acid collectors, e.g. based on salts of long-chain acids, such as e.g. calcium stearate, magnesium stearate, zinc stearate, calcium lactate or on hydrotalcites and/or stabilisers from the group of phenolic antioxidants and phosphites and/or light stabilisers from the group of hindered amines (HALS) and/or dispersants.

Suitable light stabilisers are for example compounds based on 2-(2'-hydroxyphenyl)benzotriazoles, 2-hydroxybenzophenones, esters of benzoic acids, acrylates, oxamides and 2-(2-hydroxyphenyl)-1,3,5-triazines.

Suitable 2-(2"-hydroxyphenyl)benzotriazoles are for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis($\alpha,\alpha$-dimethylbenzyl)-2'-hydroxyphenyl)benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5-methylphenyl)benzotriazole, 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazol-2-ylphenol]; the product of reesterification of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]$_2$, with R=3'-tert-butyl-4'-hydroxy-5'-2H-benzotriazol-2-ylphenyl, 2-[2'-hydroxy-3'-($\alpha,\alpha$-dimethylbenzyl)-5'-(1,1,3,3-tetramethylbutyl)phenyl]benzotriazole, 2-[2'-hydroxy-3'-(1,1,3,3-tetramethylbutyl)-5'-($\alpha,\alpha$-dimethylbenzyl)phenyl]benzotriazole.

Suitable 2-hydroxybenzophenones are for example 4-hydroxy-, 4-methoxy-, 4-octyloxy-, 4-decyloxy-4-dodecyloxy, 4-benzyloxy, 4,2',4'-trihydroxy- and 2'-hydroxy-4,4'-dimethoxy derivatives of 2-hydroxybenzophenones.

Suitable acrylates are for example ethyl-$\alpha$-cyano-$\beta,\beta$-diphenylacrylate, isooctyl-$\alpha$-cyano-$\beta,\beta$-diphenylacrylate, methyl-$\alpha$-carbomethoxycinnamate, methyl-$\alpha$-cyano-$\beta$-methyl-p-methoxycinnamate, butyl-$\alpha$-cyano-$\beta$-methyl-p-methoxycinnamate, methyl-$\alpha$-carbomethoxy-p-methoxycinnamate and N-($\beta$-carbomethoxy-$\beta$-cyanovinyl)-2-methylindoline.

Suitable esters of benzoic acids are for example 4-tert-butylphenylsalicylate, phenylsalicylate, octylphenylsalicylate, dibenzoylresorcinol, bis(4-tert-butylbenzoyl)resorcinol, benzoylresorcinol, 2,4-di-tert-butylphenyl-3,5-di-tert-butyl-4-hydroxybenzoate, hexadecyl-3,5-di-tert-butyl-4-hydroxybenzoate, octadecyl-3,5-di-tert-butyl-4-hydroxybenzoate, 2-methyl-4,6-di-tert-butylphenyl-3,5-di-tert-butyl-4-hydroxybenzoate.

Suitable oxamides are for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and the mixtures thereof with 2-ethoxy-2'-ethyl-5,4'-di-tert-butoxanilide, mixtures of o- and p-methoxy-disubstituted oxanilides and mixtures of n- and p-ethoxy-disubstituted oxanilides.

Suitable 2-(2-hydroxyphenyl)-1,3,5-triazines are for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl-1,3,5-triazine.

Suitable metal deactivators are for example N,N'-diphenyloxamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyldihydrazide, oxanilide, isophthaloyldihydrazide, sebacoylbisphenylhydrazide, N,N'-diacetyladipoyldihydrazide, N,N'-bis(salicyloyl)oxy-lyldihydrazide, N,N'-bis(salicyloyl)thiopropionyldihydrazide.

In particular, the following structures are suitable as metal deactivators:

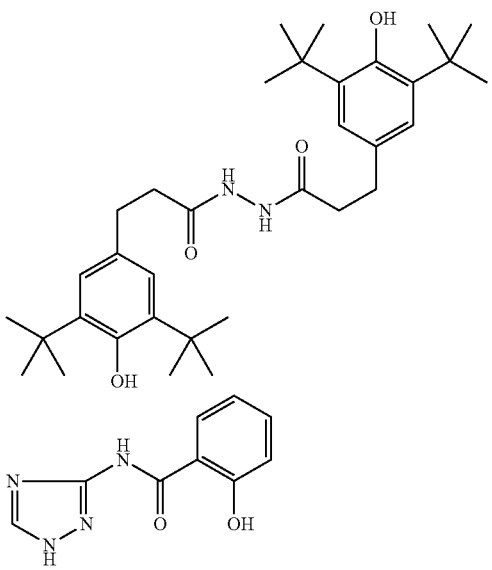

Suitable phenolic antioxidants are for example:

alkylated monophenols, such as e.g. 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-($\alpha$-methylcyclohexyl)-4,6-dimethylphenol, 2,6-dioctadecyl-4-methylphenol, 2,4,6-tricyclohexylphenol, 2,6-di-tert-butyl-4-methoxymethylphenol, linear or branched nonylphenols, such as e.g. 2,6-dinonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures hereof;

alkylthiomethylphenols, such as e.g. 2,4-dioctylthiomethyl-6-tert-butylphenol, 2,4-dioctylthiomethyl-6-methylphenol, 2,4-dioctylthiomethyl-6-ethylphenol, 2,6-didodecylthiomethyl-4-nonylphenol;

hydroquinones and alkylated hydroquinones, such as e.g. 2,6-di-tert-butyl-4-methyoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenylstearate, bis(3,5-di-tert-butyl-4-hydroxylphenyl)adipate;

tocopherols, such as e.g. $\alpha$-, $\beta$-, $\gamma$-, $\delta$-tocopherol and mixtures of these (vitamin E);

hydroxylated thiodiphenylethers, such as e.g. 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amyl-phenol), 4,4'-bis(2,6-dimethyl-4-hydroxyphenyl)disulphide;

alkylidenebisphenols, such as e.g. 2,2'-methylenebis(6-tert-butyl-4-methylphenol), 2,2'-methylenebis(6-tert-butyl-4-ethylphenol), 2,2'-methylenebis[4-methyl-6-($\alpha$-methylcyclohexyl)phenol], 2,2'-methylenebis(4-methyl-6-cyclhexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-($\alpha$-methylbenzyl)-4-nonylphenol], 2,2'-methylenebis[6-($\alpha$,$\alpha$-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl) butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol-bis[3,3-bis(3'-tert-butyl-4'-hydroxyphenyl) butyrate], bis(3-tert-butyl-4-hydroxy-5-methylphenyl)dicyclopentadiene, bis[2-(3'-tert-butyl-2'-hydroxy-5-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis-(5-tert-butyl-4-hydroxy-2-methylphenyl)-4-n-dodecylmercaptobutane, 1,1,5,5-tetra(5-tert-butyl-4-hydroxy-2-methylphenyl)pentane;

O-, N- and S-benzyl compounds, such as e.g. 3,5,3',5'-tetra-tert-butyl-4,4'-dihydroxydibenzylether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl) sulphide, isooctyl-3,5-di-tert-butyl-4-hydroxybenzylmercaptoacetate;

hydroxybenzylated malonates, such as e.g. dioctadecyl-2,2-bis(3,5-di-tert-butyl-2-hydroxybenzyl)malonate, dioctadecyl-2-(3-tert-butyl-4-hydroxy-5-methylbenzyl) malonate, didodecylmercaptoethyl-2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate;

aromatic hydroxybenzyl compounds, such as e.g. 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl) phenol;

triazine compounds, such as e.g. 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, 2,4,6-tris(3,5-di-tert-butyl-4-hydroxphenylethyl)-1,3,5-triazine, 1,3,5-tris(3,5-di-tert-butyl-4-hydroyphenylpropionyl)hexahydro-1,3,5-triazine, 1,3,5-tris(3,5-dicyclohexyl-4-hydroxybenzyl)isocyanurate;

benzylphosphonates, such as e.g. dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethylester of 3,5-di-tert-butyl-4-hydroxybenzyl-phosphonic acid;

acylaminophenols, such as e.g. 4-hydroxylauranilide, 4-hydroxystearanilide, octyl-N-(3,5-di-tert-butyl-4-hydroxyphenyl)carbamate;

esters of $\beta$-(3,5-di-tert-butyl-4-hydroxyphenyl)propionic acid with mono- or multivalent alcohols, e.g. methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane, esters of β-(5-tert-butyl-4-hydroxy-3-methylphenyl)propionic acid with mono- or multivalent alcohols, e.g. methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane, 3,9-bis[2-{3-(3-tert-butyl-4-hydroxy-5-methylphenyl)propionyloxy}-1,1-dimethylethyl]-2,4,8,10-tetraoxaspiro[5.5]undecane;

esters of β-(3,5-dicyclohexyl-4-hydroxyphenyl)propionic acid with mono- or multivalent alcohols, e.g. methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane;

esters of 3,5-di-tert-butyl-4-hydroxyphenyl)acetic acid with mono- or multivalent alcohols, e.g. methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane;

amides of β-(3,5-di-tert-butyl-4-hydroxyphenyl)propionic acid, such as e.g. N,N'-bis(3,5-di-tert-butyl-4-hydroxyphenylpropionyl)hexamethylenediamide, N,N'-bis(3,5-di-tert-butyl-4-hydroxyphenylpropionyl)hexamethylenediamide, N,N'-bis(3,5-di-tert-butyl-4-hydroxyphenylpropionyl)hexamethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1, marketed by Uniroyal);

ascorbic acid (vitamin C).

Particularly preferred phenolic antioxidants are: octadecyl-3-(3,5-di-tert-butyl-4-hydroxyphenyl)propionate, pentaerythritoltetrakis[3-(3,5-di-tert-butyl-4-hydroxyphenyl)propionate, tris(3,5-di-tert-butyl-4-hydroxyphenyl)isocyanurate, 1,3,5-trimethyl-2,4,6-tris(3,5-di-tert-butyl-4-hydroxyphenyl)isocyanurate, 1,3,5-trimethyl-2,4,6-tris(3,5-di-tert-butyl-4-hydroxybenzyl)benzene, triethyleneglycol-bis[3-(3-tert-butyl-4-hydroxy-5-methylphenyl)propionate, N,N'-hexan-1,6-diyl-bis[3-(3,5-di-tert-butyl-4-hydroxyphenyl)propionic acid amide.

Suitable phosphites/phosphonites are for example: triphenylphosphite, diphenylalkylphosphites, phenyldialkylphosphites, tri(nonylphenyl)phosphite, trilaurylphosphites, trioctadecylphosphite, distearylpentaerythritoldiphosphite, tris-(2,4-di-tert-butylphenyl)phosphite, diisodecylpentaerythritoldiphosphite, bis(2,4-di-tert-butylphenyl)pentaerythritoldiphosphite, bis(2,4-di-cumylphenyl)pentaerythritoldiphosphite, bis(2,6-di-tert-butyl-4-methylphenyl)pentaerythritoldiphosphite, diisodecyloxypentaerythritoldiphosphite, bis(2,4-di-tert-butyl-6-methylphenyl)pentaerythritoldiphosphite, bis(2,4,6-tris(tert-butylphenyl)pentaerythritoldiphosphite, tristearylsorbitoltriphosphite, tetrakis(2,4-di-tert-butylphenyl)-4,4-biphenylenediphosphonite, 6-isooctyloxy-2,4,8,10-tetra-tert-butyl-12H-dibenzo[d,g]-1,3,2-dioxaphosphocine, bis(2,4-di-tert-butyl-6-methylphenyl)methylphosphite, bis(2,4-di-tert-butyl-6-methylphenyl)ethylphosphite, 6-fluoro-2,4,8,10-tetra-tert-butyl-12-methyl-dibenzo[d,g]-1,3,2-dioxaphosphocine, 2,2'2"-nitrilo[triethyltris(3,3",5,5'-tetra-tert-butyl-1,1'-biphenyl-2,2'-diyl)phosphite], 2-ethylhexyl(3,3',5,5'-tetra-tert-butyl-1,1'-biphenyl-2,2'-diyl))phosphite, 5-butyl-5-ethyl-2-(2,4,6-tri-tert-butylphenoxy)-1,3,2-dioxaphosphirane.

Particularly preferred phosphites/phosphonites are:

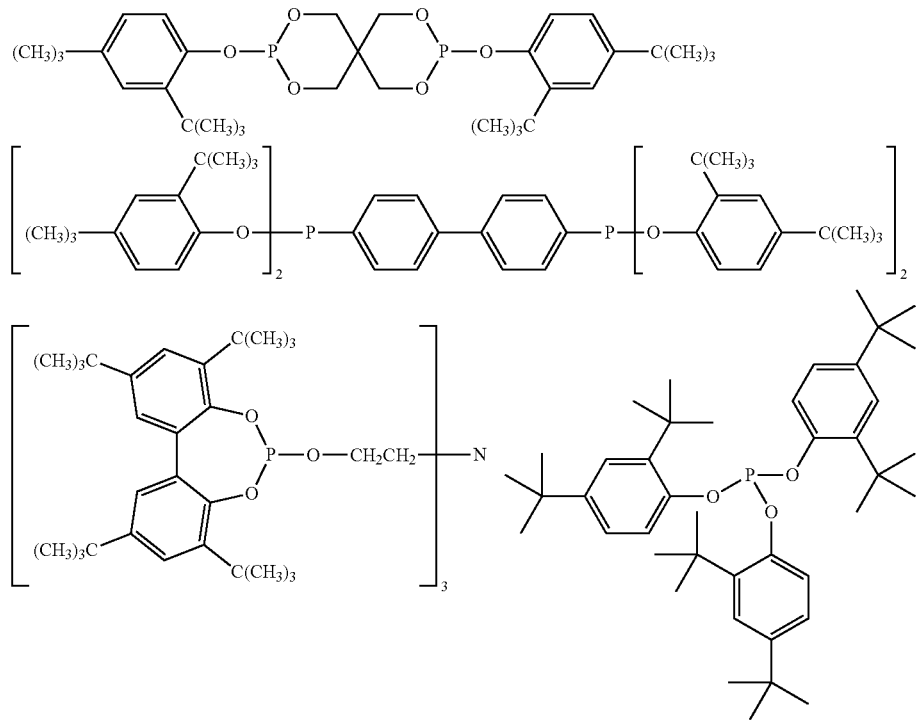

-continued
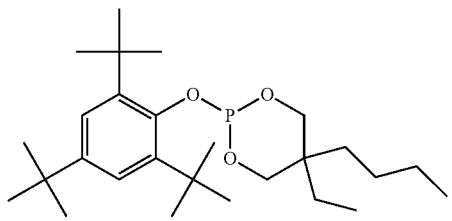
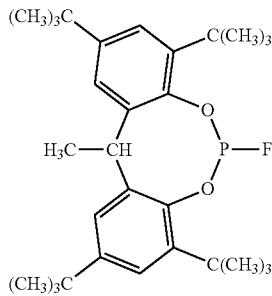
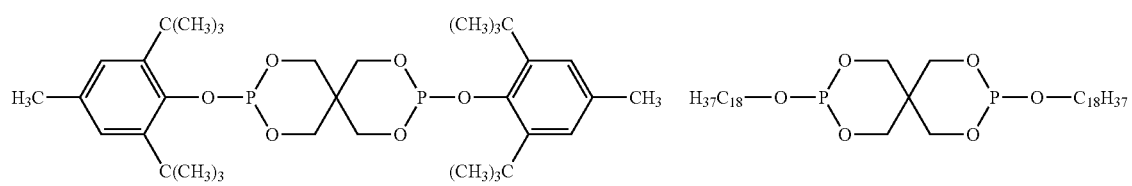
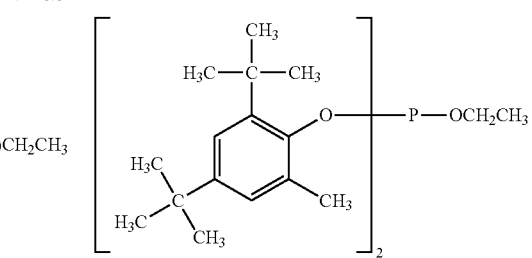
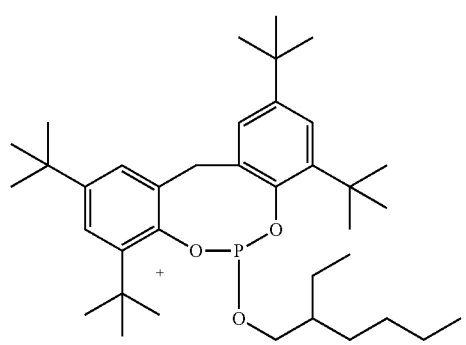
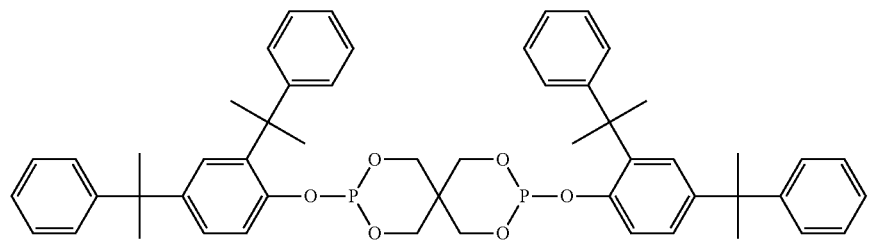
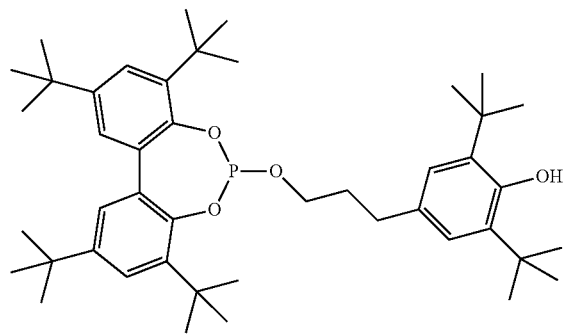

Further suitable stabilisers are aminic antioxidants. Suitable aminic antioxidants are for example:

N,N'-diisopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulphamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, e.g. p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazine, N,N,N',N'-tetraphenyl-1,4-diaminobut-2-ene and also mixtures or combinations hereof.

Further suitable aminic antioxidants are hydroxylamines or N-oxides (nitrons), such as e.g. N,N-dialkylhydroxylamines, N,N-dibenzylhydroxylamine, N,N-dilaurylhydroxylamine, N,N-distearylhydroxylamine, N-benzyl-α-phenylnitron, N-octadecyl-α-hexadecylnitron, and also Genox EP (Addivant) according to the formula:

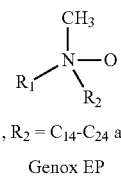

R$_1$, R$_2$ = C$_{14}$-C$_{24}$ alkyl

Genox EP

Further suitable stabilisers are thiosynergists. Suitable thiosynergists are, for example, distearylthiodipropionate, dilauryldipropionate or the compound according to the following formula:

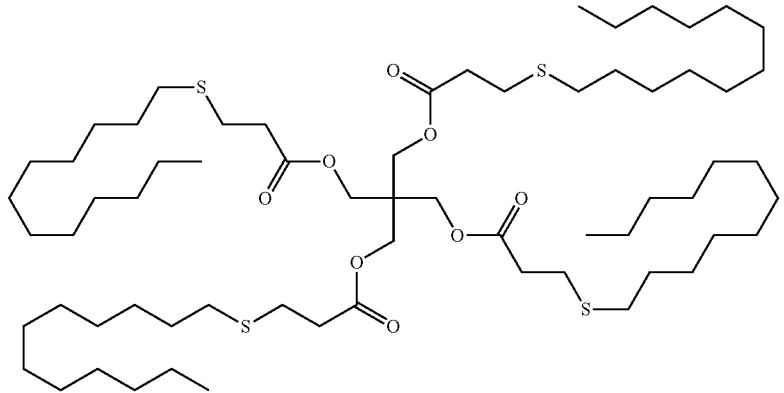 [SMILES: CCCCCCCCCCCCSCCC(=O)OCC(COC(=O)CCSCCCCCCCCCCCC)(COC(=O)CCSCCCCCCCCCCCC)COC(=O)CCSCCCCCCCCCCCC]

Further suitable stabilisers, in particular for polyamides, are copper salts, such as e.g. copper(I)iodide, copper(I) bromide or copper complexes, such as e.g. triphenylphosphine-copper(I) complexes.

Suitable hindered amines are for example 1,1-bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl)-n-butyl-3,5-di-tert-butyl-4-hydroxybenzylmalonate, the condensation product of 1-(2-hydroxyethyl)-2,2,6,6-tetramethyl-4-hydroxypiperidine and succinic acid, linear or cyclic condensation products of N,N'-bis(2,2,6,6-tetramethyl-4-piperidyl)hexamethylenediamine and 4-tert-octylamino-2,6-dichloro-1,3,5-triazine, tris (2,2,6,6-tetramethyl-4-piperidyl)nitrilotriacetate, tetrakis(2,2,6,6-tetramethyl-4-piperidyl)-1,2,3,4-butanetetracarboxylate, 1,1'-(1,2-ethandiyl)-bis(3,3,5,5-tetramethylpiperazinone), 4-benzoyl-2,2,6,6-tetramethylpiperidine, 4-stearyloxy-2,2,6,6-tetramethylpiperidine, linear or cyclic condensation products of N,N'-bis(2,2,6,6-tetramethyl-4-piperidyl)hexamethylenediamine and 4-morpholino-2,6-dichloro-1,3,5-triazine, the reaction product of 7,7,9,9-tetramethyl-2-cycloundecyl-1-oxa-3,8-diaza-4-oxospiro-[4,5]decane und epichlorohydrin.

Suitable dispersants are for example:

polyacrylates, e.g. copolyers with long-chain side groups, polyacrylate block copolymers, alkylamides: e.g. N,N'-1,2-ethandiylbisoctadecaneamide sorbitan ester, e.g. monostearyl sorbitan ester, titanates und zirconates, reactive copolymers with functional groups, e.g. polypropylene-co-acrylic acid, polypropylene-co-maleic anhydride, polyethylene-co-glycidylmethacrylate, polystyrene-alt-maleic anhydride-polysiloxanes: e.g. dimethylsilanediol-ethylene oxide copolymer, polyphenylsiloxane copolymer, amphiphilic copolymers: e.g. polyethylene-block-polyethylene oxide, dendrimers, e.g. hydroxyl group-containing dendrimers.

Suitable nucleation agents are for example talc, alkali or alkaline earth salts of mono- and polyfunctional carboxylic acids, such as e.g. benzoic acid, succinic acid, adipic acid, e.g. sodium benzoate, zinc glycerolate, aluminium hydroxybis(4-tert-butyl)benzoate, benzylidenesorbitols, such as e.g.

1,3:2,4-bis(benzylidene)sorbitol or 1,3:2,4-bis(4-methylbenzylidene)sorbitol, 2,2'-methylene-bis-(4,6-di-tert-butylphenyl)phosphate, and also trisamides, such as e.g according to the following structures

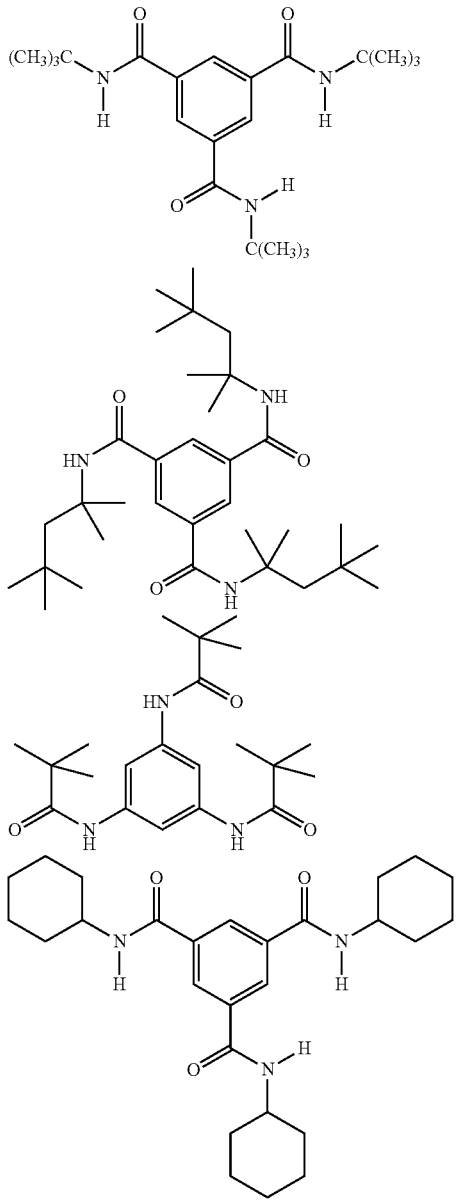

Suitable fillers and reinforcing materials are for example synthetic or natural materials, such as e.g. calcium carbonate, silicates, glass fibres, glass balls (solid or hollow), talc, mica, kaolin, barium sulphate, metal oxides and metal hydroxides, carbon black, graphite, carbon nanotubes, graphene, sawdust or fibres of natural products, such as e.g. cellulose, or synthetic fibres. Further suitable fillers are hydrotalcites or zeolites or layer silicates, such as e.g. montmorrillonite, bentonite, beidelite, mica, hectorite, saponite, vermiculite, ledikite, magadite, illite, kaolinite, wollastonite, attapulgite.

Suitable pigments can be of an inorganic or organic nature. Inorganic pigments are for example titanium dioxide, zinc oxide, zinc sulphide, iron oxide, ultramarine, carbon black, organic pigments are for example anthraquinones, anthanthrones, benzimidazolones, quinacridones, diketopyrrolopyrroles, dioxazines, indanthrones, isoindolinones, azo compounds, perylenes, phthalocyanines or pyranthrones. Further suitable pigments are effect pigments based on metal or pearlescent pigments based on metal oxide.

Suitable chain lengtheners for the linear molecular weight increase of polycondensation polymers such as polyesters or polyamides are for example diepoxides, bis-oxazolines, bizoxazolones, bis-oxazines, diiosocyanates, dianhydrides, bisacyllactams, bis-maleimides, dicyanates, carbodiimides. Further suitable chain lengtheners are polymeric compounds, such as e.g. polystyrene-polyacrylate-polyglicidyl (meth)acrylate copolymers, polystyrene-maleic anhydride copolymers and polyethylene-maleic anhydride copolymers.

Optical brighteners are for example bisbenzoxazoles, phenylcumarines or bis(styryl)biphenyls and in particular optical brighteners of the formulae:

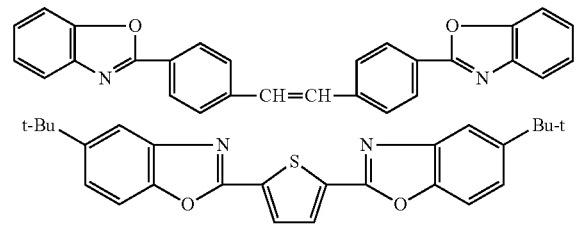

Suitable filler deactivators are for example glycidyl-based epoxides, such as e.g. bisphenol-A-diglycidylether or bisphenol-F-diglycidylether and the oligomeric or polymer resins thereof, polysiloxanes, polyacrylates, in particular block copolymers, such as polymethacrylic acid-polyalkylene oxide.

Suitable antistatic agents are for example ethoxylated alkylamines, fatty acid esters, alkyl sulphonates and polymers, such as e.g. polyether amides.

Furthermore, the present invention relates to a method for the production of a previously described, flame-retardant and/or stabilised, in particular (photo)oxidatively stabilised, plastic material composition, in which there is introduced a) 0.1 to 40 parts by weight, preferably 1 to 25, particularly preferably 2.5 to 15 parts by weight, of at least one phosphorus-containing organic oxyimide, comprising at least one structural element of the subsequently illustrated formula I,

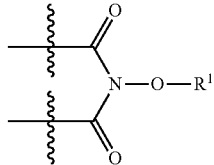

Formula I b) before, after or at the same time, with 0 to 25 parts by weight, preferably 2.5 to 15 parts by weight, of at least one further flame retardant in 60 to 99.9 parts by weight, preferably 60 to 98, particularly preferably 70 to 95 parts by weight, of at least one plastic material, in particular of at least one thermoplastic polymer.

With respect to the preferably useable phosphorus-containing organic oxyimides, reference is made to the previously given explanations.

A further subject of the present invention is a moulded part, paint or coating producible from a previously described flame-retardant plastic material composition, in particular in the form of injection moulded parts, foils, coatings, foams, fibres, cables and pipes, which are produced via extrusion, injection moulding, blow-moulding, pressing processes, e.g. for household and electrical appliances, vehicle parts, consumer articles, furniture, textiles.

The flame retardants used according to the invention are suitable in particular for thermoplastic, elastomeric and duromeric plastic materials, in particular in the form of injection moulded parts, foils or films, coatings or paints, foams, fibres, cables and pipes, profiles, hollow bodies, strips, membranes, such as e.g. geomembranes, or adhesives, which are produced via extrusion, injection moulding, blow-moulding, calendering, pressing processes, spinning processes, roto-moulding or brushing and coating processes, e.g. for the electrical and electronics industry, construction industry, transport industry (cars, aircraft, ships, trains), for medical applications, for household and electrical appliances, vehicle parts, consumer articles, packaging, furniture, textiles. A further field of use is varnishes, paints and coatings.

Particularly preferred examples of phosphorus-containing organic oxyimides which can be used according to the present invention or can be contained in the flame-retardant plastic material compositions are subsequently illustrated, without however limiting the previously illustrated invention to these special structures:

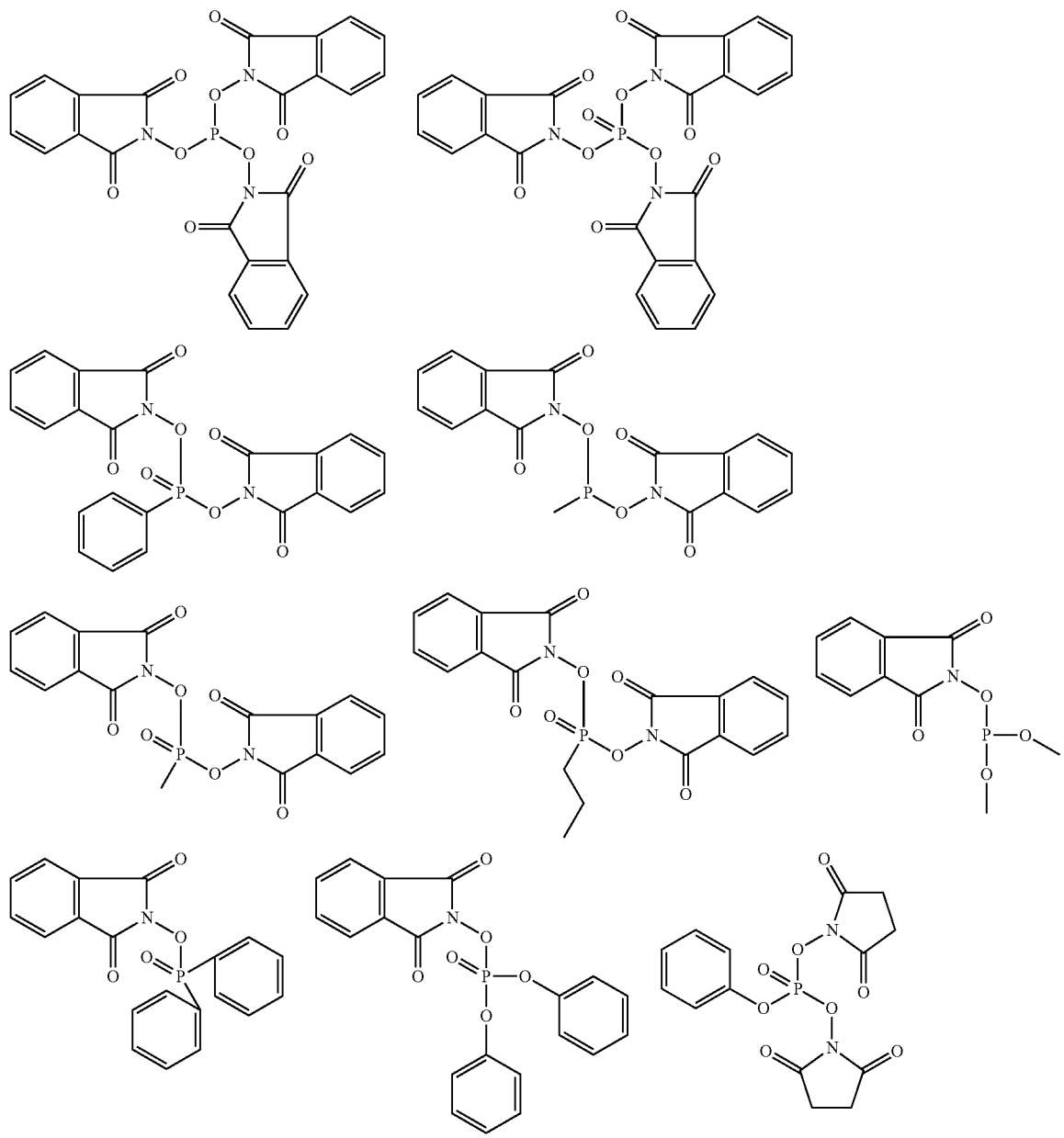

-continued
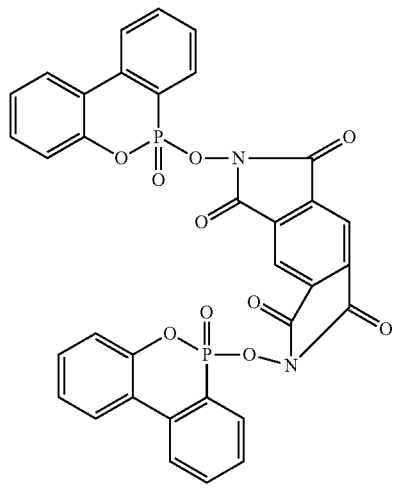
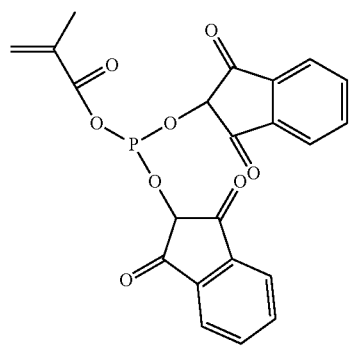
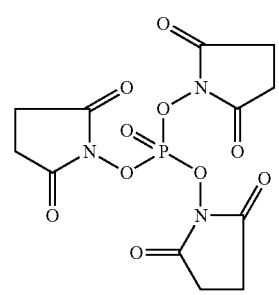
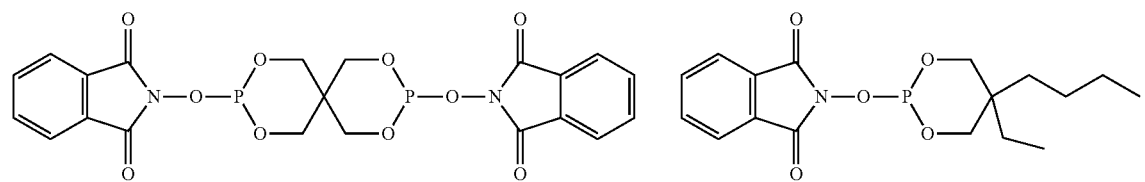
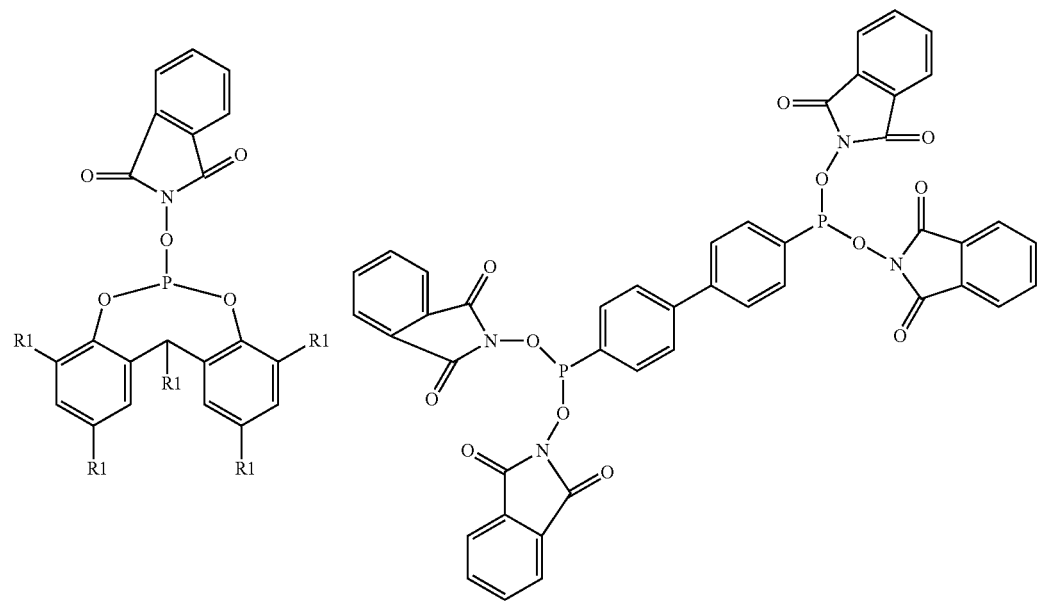

Possibly the phosphorus-containing oxyimides according to the invention can also have polymeric structures, such as e.g. with the following recurring units:

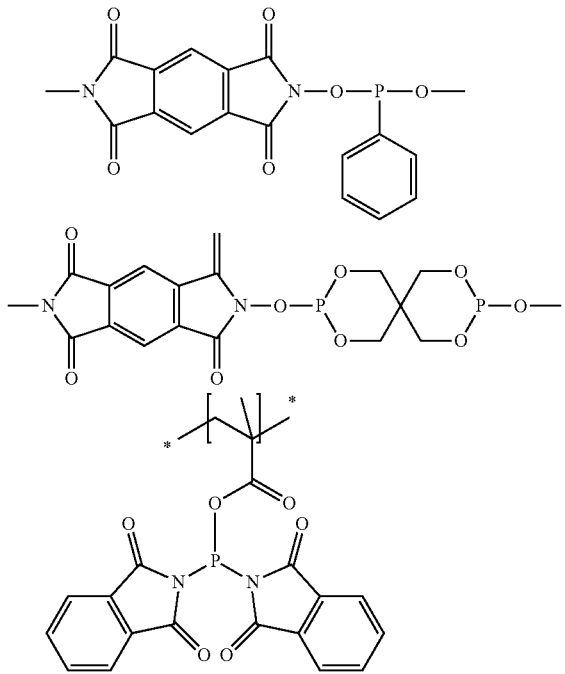

Incorporation of the above-described flame retardants and of the additional additives in the plastic material is effected by normal processing methods, the polymer being melted and mixed with the flame retardants and additives, preferably by mixers, kneaders and extruders. As processing machines, extruders, such as e.g. single-screw extruders, twin-screw extruders, planet roller extruders, ring extruders, co-kneaders, which are preferably equipped with vacuum degassing, are preferred. The processing can thereby be effected under air or possibly under inert gas conditions. Different flame retardants and additives can be added thereby separately or as a mixture, in the form of liquids, powders, granulates or compacted products or likewise in the form of master batches or concentrates which comprise for example 50-80% of the compositions according to the invention.

The present invention is explained in more detail with reference to the following examples, without restricting the invention thereto.

A) Syntheses of Phosphorus-Containing Oxyimides According to the Invention

SYNTHESIS EXAMPLE 1

Synthesis of phosphoryl-tris-N-oxyphthalimide

There is added drop-wise to a dispersion of sodium N-oxyphthalimide (18.41 g; 9.9 mmol) in absolute THF (125 ml) under inert gas, phosphoryl chloride (3.0 ml; 3.3 mmol) and the mixture is subsequently agitated for two days, the result being decolouration of the dispersion. The insoluble components are separated by filtration and the mixture comprising the product is obtained without further cleaning after removal of the solvent on a rotary evaporator.

$^1$H-NMR (500 MHz, DMSO): δ=7.82 (S) ppm.

$^{13}$C-NMR (126 MHz, DMSO): δ=164.05, 134.47, 128.73, 122.91, 39.52 ppm.

$^{31}$P-NMR (202 MHz, DMSO): δ=0.31, −11.76 ppm.

SYNTHESIS EXAMPLE 2

Synthesis of phenoxyphosphoryl-bis-N-oxyphthalimide

There is added drop-wise to a dispersion of sodium N-oxyphthalimide (18.0 g; 9.7 mmol) in absolute THF (125 ml) under inert gas, phenyldichlorophosphate (7.1 ml; 4.7 mmol) and the mixture is subsequently agitated for two days, the result being decolouration of the dispersion. The insoluble components are separated by filtration and the mixture comprising the product is obtained without further cleaning after removal of the solvent on a rotary evaporator.

$^1$H-NMR (300 MHz, DMSO); δ=7.82 (S), 7.33-7.31 (m)
$^{31}$P-NMR (122 MHz, DMSO); δ=−6.58.

SYNTHESIS EXAMPLE 3

Synthesis of a 10-chloro-9,10-dihydro-9-oxa-10-phosphaphenanthrene-N-hydroxyphthalimide adduct There is added dropwise to a solution of N-hydroxyphthalimide (6.95 g; 42.6 mmol) and triethylamine (5.9 ml; 42 mmol) in absolute THF (100 ml), a solution of 10-chloro-9,10-dihydro-9-oxa-10-phosphaphenathrene (10 g; 42.6 mmol) in absolute THF (50 ml) and the mixture is subsequently agitated for 12 hours at ambient temperature, the result being decolouration of the solution. After the end of the reaction, the product is filtered off, washed with water and subsequently obtained as a pure product by recrystallisation in toluene.

$^1$H NMR (300 MHz, CDCl$_3$): δ=8.27 (ddd, J=7.7, 1.5, 0.6 Hz, 1H), 8.05 (d, J=8.0 Hz, 1H), 7.99 (dd, J=8.0, 1.6 Hz, 1H), 7.86-7.80 (m, 2H), 7.80-7.77 (m, 1H), 7.77-7.71 (m, 2H), 7.59 (td, J=7.6, 1.0 Hz, 1H), 7.45, (ddd, J=8.5, 7.0, 1.6 Hz, 1H), 7.39-7.34 (m, 1H), 7.31 (ddd, J=8.0, 7.1, 1.6 Hz, 1H).

$^{31}$P NMR (122 MHz, CDCl$_3$): δ=2.58.

SYNTHESIS EXAMPLE 4

Synthesis of diphenoxyphosphoryl-N-oxyphthalimide

There is added drop-wise to a solution of N-hydroxyphthalimide (15.18 g; 93 mmol) and triethylene (13 ml; 93 mmol) in absolute DCM (400 ml), diphenoxyphosphoryl chloride (19.3 g; 93 mmol) and the mixture is subsequently agitated for 12 hours at ambient temperature, the result being decolouration of the solution. After the end of the reaction, the solution is washed three times with respectively 200 ml of water and subsequently with 200 ml of 10% NaHCO$_3$ solution. After drying over calcium chloride and removal of the solvent, the product is obtained by recrystallisation in DCM/hexane 1:1.

$^1$H-NMR (300 MHz, CDCl$_3$): δ=7.93-7.85 (m, 2H), 7.85-7.76 (m, 2H), 7.48-7.36 (m, 8H), 7.36-7.20 (m, 2H).
$^{31}$P-NMR (122 MHz, CDCl$_3$): δ=−11.68 ppm.

B) Production and Testing of a Flame-Retardant Plastic Material Mixture According to the Invention The extrusions of the polypropylene samples (DOW C766-03) are effected at a temperature of 190° C. and a screw speed of rotation of 150 rpm on an 11 mm twin-screw extruder (Process 11 of Thermo Scientific). The desired ratio of polymer and additives is firstly homogenised by mixing and supplied to the extrusion via volumetric metering.

Test pieces for the fire test are produced from the granulate at a temperature of 220° C. and a pressure of 2 t using a hydraulic 10 t press (Werner & Pfleiderer). For this purpose, the granulate is filled into the compression mould and this is transferred into the already preheated press. At a pressure of 0.5 t, the granulate is firstly melted for 60 s. After expiry of the melting time, the pressure is increased to 2 t and kept constant for a further 3 min. Whilst maintaining the contact pressure, the mould is cooled to 60° C. and thereafter the test pieces are removed. The test pieces have the following dimensions according to the standard: 127.5×12.5× 1.5.

The examples and comparative examples according to the invention contained in Table 1 were tested according to DIN EN 60695-11-10 and the burning times and classification according to the standard were obtained:

TABLE 1

Compositions in polypropylene and results of the fire test

| Example | Composition Flame retardant | Burning times Total of the secondary burning times of 5 test pieces with 2 flame impingements [in seconds] | Classification according to DIN EN 60695-11-10 |
|---|---|---|---|
| Comparative example 1 (state of the art) | 15% aluminium diethyl-phosphinate | >200 | not classified |
| Comparative example 2 | 20% aluminium diethyl-phosphinate | 170 | not classified |
| Example 1 according to the invention | 15% aluminium diethyl-phosphinate 2% phosphoryl-tris-N-oxy-phthalimide (synthesis example 1) | 21.8 | V-2 |
| Example 2 according to the invention | 15% aluminium diethyl-phosphinate 2% phenoxyphosphoryl-bis-N-oxy-phthalimide (synthesis example 2) | 47.2 | V-2 |
| Example 3 according to the invention | 6% aluminium diethyl-phosphinate 4% phenoxyphosphoryl-bis-N-oxy-phthalimide (synthesis example 2) | 16.5 | V-2 |
| Example 4 according to the invention | 15% diethyl-aluminium phosphinate 2% 10-choro-9,10-dihydro-9-oxa-10-phosphaphen-anthrene N-hydroxyphthal-imide adduct (synthesis example 3) | 83.8 | V-2 |
| Example 5 according to the invention | 15% diethyl-aluminium phosphinate 2% diphenoxy-phosphoryl-N-oxyphthalimide (synthesis example 4) | 23.9 | V-2 |
| Example 6 according to the invention | 10% diethyl-aluminium phosphinate 5% diphenoxy-phosphoryl-N-oxyphthalimide (synthesis example 4) | 19.9 | V-2 |

Aluminium diethylphosphinate (Exolit OP 1230, manufacturer: Clariant SE)

The examples according to the invention are self-extinguishing after removal of the source of ignition and have surprisingly reduced burning times relative to the comparative example, a classification according to V-2 is obtained.

The invention claimed is:

1. A method of imparting flame retardancy, stability, and/or oxidation resistance to a plastic material comprising incorporating into the plastic material a phosphorus-containing organic oxyimide containing at least one structural element of Formula I

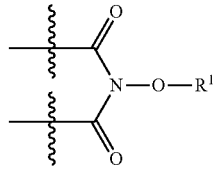

Formula I wherein $R^1$ is selected from the group consisting of phosphorus-containing radicals;

wherein the structural element according to Formula I is part of a polymer or copolymer, the polymer or copolymer having at least one of the following repeat units:

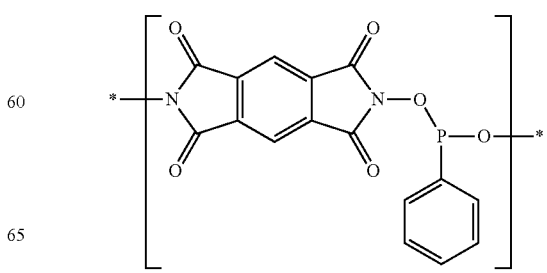

-continued

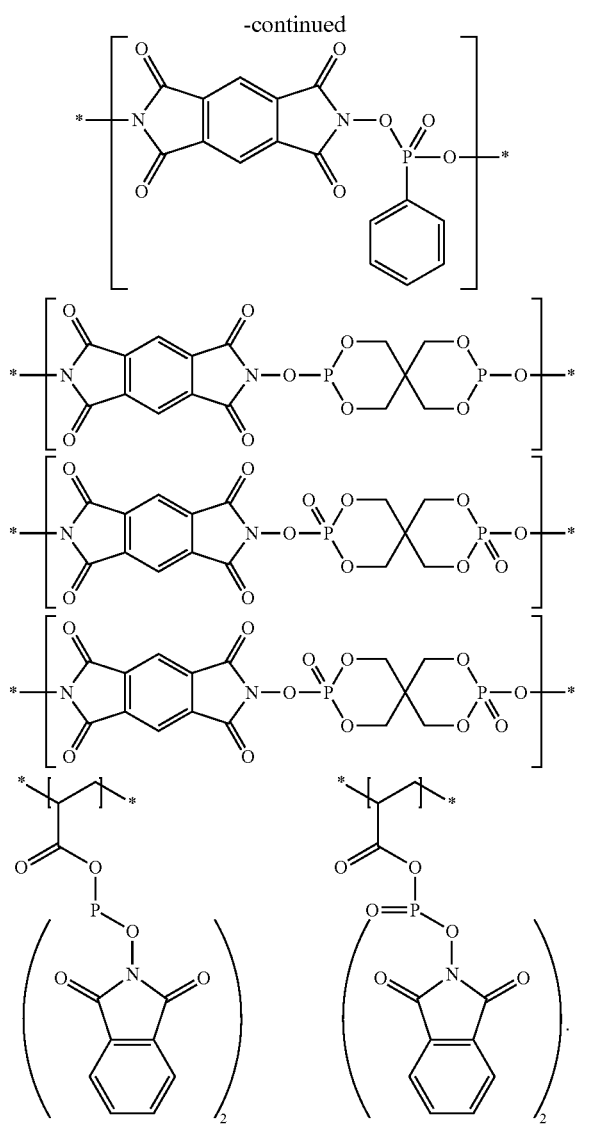

2. The method according to claim 1, wherein the plastic material is a thermoplastic polymer selected from the group consisting of
   a) polymers made of olefins or diolefins,
   b) polystyrene, polymethylstyrene, polyvinylnaphthalene, styrene-butadiene (SB), styrene-butadiene-styrene (SBS), styrene-ethylene-butylene-styrene (SEBS), styrene-ethylene-propylene-styrene, styrene-isoprene, styrene-isoprene-styrene (SIS), styrene-butadiene-acrylonitrile (ABS), styrene-acrylonitrile-acrylate (ASA), styrene-ethylene, styrene-maleic anhydride polymers including corresponding graft copolymers, graft copolymers made of methylmethacrylate, styrene-butadiene and ABS (MABS),
   c) halogen-containing polymers,
   d) polymers of unsaturated esters, polyacrylonitrile, polyacrylamides, copolymers, and polymethacrylimide,
   e) polymers made of unsaturated alcohols and derivatives,
   f) polyacetals,
   g) polyphenylene oxides and blends with polystyrene or polyamides,
   h) polymers of cyclic ethers,
   i) polyurethanes made of hydroxy-terminated polyethers or polyesters and aromatic or aliphatic isocyanates, and polyureas,
   j) polyamides, blends of different polyamides, and blends of polyamides and polyolefins,
   k) polyimides, polyamideimides, polyetherimides, polyesterimides, poly(ether)ketones, polysulphones, polyethersulphones, polyarylsulphones, polyphenylene sulphide, polybenzimidazoles, and polyhydantoins,
   l) polyesters made of aliphatic or aromatic dicarboxylic acids and diols or made of hydroxycarboxylic acids,
   m) polycarbonates, polyester carbonates and blends thereof,
   n) cellulose derivatives,
   o) duromeric or elastomeric, non-thermoplastic plastic materials, and
   p) mixtures, combinations or blends of two or more of the previously mentioned polymers.

3. The method according to claim 1, wherein the phosphorus-containing organic oxyimide is incorporated in combination with at least one further flame retardant, selected from the group consisting of
   a) inorganic flame retardants,
   b) nitrogen-containing flame retardants,
   c) radical formers,
   d) phosphorus-containing flame retardants,
   e) halogen-containing flame retardants based on chlorine and bromine, optionally in combination with $Sb_2O_3$ and/or $Sb_2O_5$,
   f) borates, optionally placed on silica as carrier material,
   g) sulphur-containing compounds,
   h) antidrip agents,
   i) silicon-containing compounds,
   j) carbon modifications,
   and combinations or mixtures thereof.

4. The method according to claim 3, wherein the radical formers are selected from the group consisting of
   a) N-alkoxyamines according to the structural formula,

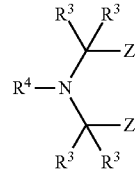

wherein
$R^3$ is hydrogen or optionally substituted alkyl-, cycloalkyl-, aryl-, heteroaryl- or acyl radical,
$R^4$ is alkoxy-, aryloxy-, cycloalkoxy-, aralkoxy- or acyloxy radical, and
Z is hydrogen or optionally substituted alkyl-, cycloalkyl-, aryl-, heteroaryl- or acyl radical, the two radicals Z also being able to form a closed ring which can be substituted optionally by ester-, ether-, amine-, amide-, carboxy- or urethane groups,
b) azo compounds according to the formula:

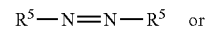 or

-continued

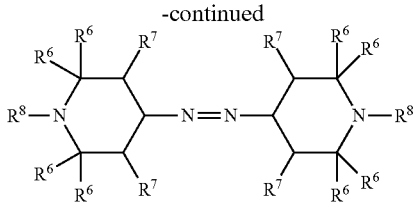

wherein

R⁵ is an alkyl, cycloalkyl- or aryl radical,

R⁶ upon each occurrence, is the same or different and meaning a linear or branched alkyl radical, R⁷ upon each occurrence, is the same or different and meaning hydrogen or a linear or branched alkyl radical, and R⁸ upon each occurrence, is the same or different and meaning an alkyl-, alkoxy-, aryloxy-, cycloalkyloxy-, aralkoxy- or acyloxy radical, c) dicumyl according to the formula

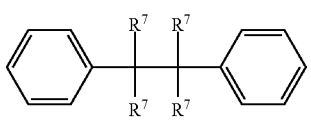

wherein R⁷ having the previously indicated meaning, and d) polycumyl according to the formula

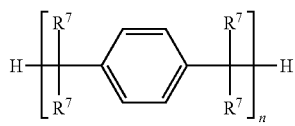

wherein R⁷ is as defined above, and 2<n<100.

5. The method according to claim 3, wherein the phosphorus-containing organic oxyimide and the at least one further flame retardant are incorporated in a weight ratio of 99:1 to 1:99.

6. The method according to claim 1, wherein the phosphorus-containing organic oxyimide, relative to the plastic materials, is incorporated at 0.01 to 30% by weight.

7. The method for the production of a flame-retardant and/or stabilised plastic material composition according to claim 1, comprising incorporating a) 0.1 to 40 parts by weight of the at least one phosphorus-containing organic oxyimide, and b) before, after or at the same time, 0 to 25 parts by weight, of at least one further flame retardant in 60 to 99.9 parts by weight, of at least one plastic material.

8. A flame-retardant and/or stabilised plastic material composition, comprising or consisting of:

a) 60 to 99.9 parts by weight, of at least one plastic material, b) 0.1 to 40 parts by weight, of at least one phosphorus-containing organic oxyimide, containing at least one structural element of Formula I,

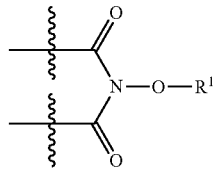

c) 0 to 25 parts by weight of at least one further flame retardant, and/or d) 0 to 25 parts by weight of at least one phosphorus-containing compound;

wherein R¹ is selected from the group consisting of phosphorus-containing radicals;

wherein the structural element according to Formula I is part of a polymer or copolymer, the polymer or copolymer having at least one of the following repeat units:

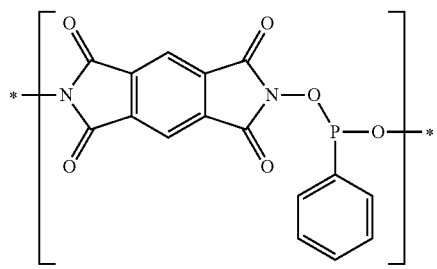

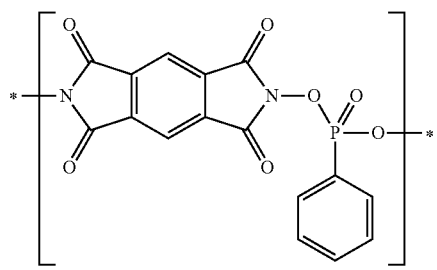

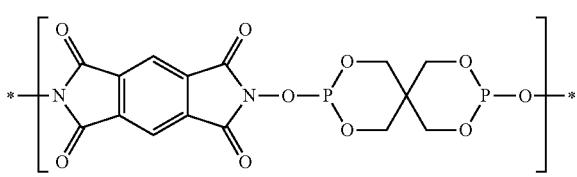

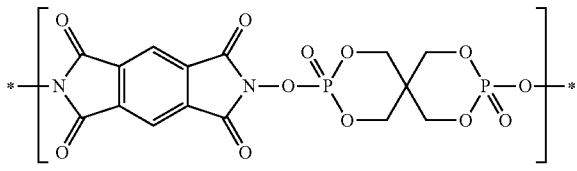

-continued

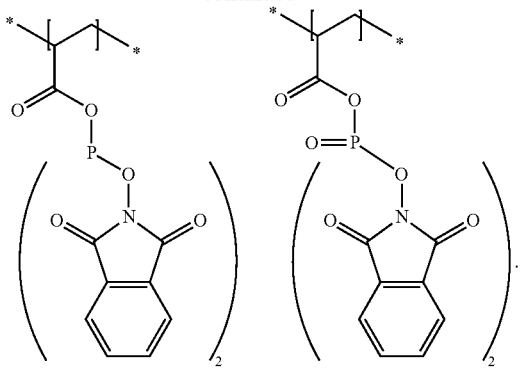

9. The flame-retardant and/or stabilised plastic material composition according to claim 8, which further includes:
   a) up to 40 parts by weight of at least one reinforcing- or filling material and/or
   b) up to 5 parts by weight of at least one additive from the class of phenolic antioxidants, phosphites, acid collectors, hindered amines, dispersants and combinations thereof.

10. The flame-retardant and/or stabilised plastic material composition according to claim 8, further comprising at least one additive selected from the group consisting of UV absorbers, light stabilisers, stabilisers, hydroxylamines, benzofuranones, nucleation agents, impact strength enhancers, plasticisers, lubricants, rheology modifiers, processing aids, pigments, colourants, optical brighteners, antimicrobial active substances, antistatic agents, slip agents, antiblocking agents, coupling means, dispersants, compatibilisers, oxygen collectors, acid collectors, marking means and antifogging means.

11. A moulded part, paint, or coating, produced from a flame-retardant plastic material composition according to claim 8.

12. A method of imparting flame retardancy, stability, and/or oxidation resistance to a plastic material comprising incorporating into the plastic material a phosphorus-containing organic oxyimide and at least one further flame retardant,
   wherein the phosphorus-containing organic oxyimide has an organic phosphite moiety or an organic phosphonite moiety.

13. The method according to claim 12, wherein the plastic material is a thermoplastic polymer selected from the group consisting of
   a) polymers made of olefins or diolefins,
   b) polystyrene, polymethylstyrene, polyvinylnaphthalene, styrene-butadiene (SB), styrene-butadiene-styrene (SBS), styrene-ethylene-butylene-styrene (SEBS), styrene-ethylene-propylene-styrene, styrene-isoprene, styrene-isoprene-styrene (SIS), styrene-butadiene-acrylonitrile (ABS), styrene-acrylonitrile-acrylate (ASA), styrene-ethylene, styrene-maleic anhydride polymers including corresponding graft copolymers, graft copolymers made of methylmethacrylate, styrene-butadiene and ABS (MABS),
   c) halogen-containing polymers,
   d) polymers of unsaturated esters, polyacrylonitrile, polyacrylamides, copolymers, and polymethacrylimide,
   e) polymers made of unsaturated alcohols and derivatives,
   f) polyacetals,
   g) polyphenylene oxides and blends with polystyrene or polyamides,
   h) polymers of cyclic ethers,
   i) polyurethanes made of hydroxy-terminated polyethers or polyesters and aromatic or aliphatic isocyanates, and polyureas,
   j) polyamides, blends of different polyamides, and blends of polyamides and polyolefins,
   k) polyimides, polyamideimides, polyetherimides, polyesterimides, poly(ether)ketones, polysulphones, polyethersulphones, polyarylsulphones, polyphenylene sulphide, polybenzimidazoles, and polyhydantoins,
   l) polyesters made of aliphatic or aromatic dicarboxylic acids and diols or made of hydroxycarboxylic acids,
   m) polycarbonates, polyester carbonates and blends thereof,
   n) cellulose derivatives,
   o) duromeric or elastomeric, non-thermoplastic plastic materials, and
   p) mixtures, combinations or blends of two or more of the previously mentioned polymers.

14. The method according to claim 12, wherein the phosphorus-containing organic oxyimide is incorporated in combination with at least one further flame retardant, selected from the group consisting of
   a) inorganic flame retardants,
   b) nitrogen-containing flame retardants,
   c) radical formers,
   d) phosphorus-containing flame retardants,
   e) halogen-containing flame retardants based on chlorine and bromine, optionally in combination with $Sb_2O_3$ and/or $Sb_2O_5$,
   f) borates, optionally placed on silica as carrier material,
   g) sulphur-containing compounds,
   h) antidrip agents,
   i) silicon-containing compounds,
   j) carbon modifications, and combinations or mixtures thereof.

15. The method according to claim 14, wherein the radical formers are selected from the group consisting of
   a) N-alkoxyamines according to the formula,

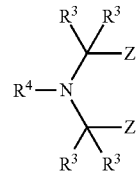

wherein
$R^3$ is hydrogen or optionally substituted alkyl-, cycloalkyl-, aryl-, heteroaryl- or acyl radical,
$R^4$ is alkoxy-, aryloxy-, cycloalkoxy-, aralkoxy- or acyloxy radical, and
Z is hydrogen or optionally substituted alkyl-, cycloalkyl-, aryl-, heteroaryl- or acyl radical, the two radicals Z also being able to form a closed ring which can be substituted optionally by ester-, ether-, amine-, amide-, carboxy- or urethane groups,
b) azo compounds according to the formula:

-continued

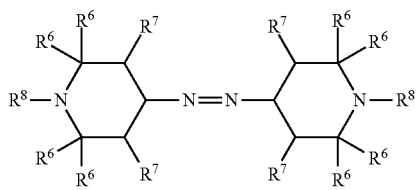

wherein

R⁵ is an alkyl, cycloalkyl- or aryl radical,

R⁶ upon each occurrence, is the same or different and meaning a linear or branched alkyl radical, R⁷ upon each occurrence, is the same or different and meaning hydrogen or a linear or branched alkyl radical, and R⁸ upon each occurrence, is the same or different and meaning an alkyl-, alkoxy-, aryloxy-, cycloalkyloxy-, aralkoxy- or acyloxy radical, c) dicumyl according to the formula

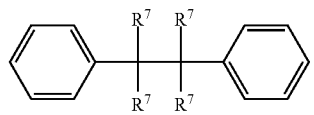

wherein $R^7$ having the previously indicated meaning, and d) polycumyl according to the formula $$H\left[\begin{array}{c} R^7 \\ | \\ -C- \\ | \\ R^7 \end{array} \bigcirc \begin{array}{c} R^7 \\ | \\ -C- \\ | \\ R^7 \end{array}\right]_n H$$

wherein $R^7$ is as defined above, and $2<n<100$.

16. The method according to claim 12, wherein the phosphorus-containing organic oxyimide and the at least one further flame retardant are incorporated in a weight ratio of 99:1 to 1:99.

* * * * *